United States Patent
Roffey et al.

(10) Patent No.: US 7,166,613 B2
(45) Date of Patent: Jan. 23, 2007

(54) CONDENSED INDOLINE DERIVATIVES AND THEIR USE AS 5HT, IN PARTICULAR $5HT_{2C}$, RECEPTOR LIGANDS

(75) Inventors: Jonathan Richard Anthony Roffey, Wokingham (GB); James Edward Paul Davidson, Wokingham (GB); Howard Langham Mansell, Wokingham (GB); Richard John Hamlyn, Wokingham (GB); David Reginald Adams, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 11/117,459

(22) Filed: Apr. 29, 2005

(65) Prior Publication Data
US 2005/0187282 A1 Aug. 25, 2005

Related U.S. Application Data

(62) Division of application No. 10/009,567, filed as application No. PCT/GB00/03008 on Aug. 4, 2000, now Pat. No. 6,962,939.

(30) Foreign Application Priority Data

Aug. 11, 1999 (GB) .................................. 9918965.5

(51) Int. Cl.
A61K 31/437 (2006.01)
C07D 471/14 (2006.01)
(52) U.S. Cl. ........................................ 514/292; 546/84
(58) Field of Classification Search .................. 546/84; 514/292
See application file for complete search history.

(56) References Cited

U.S. PATENT DOCUMENTS

| | | | |
|---|---|---|---|
| 2,541,211 A | 2/1951 | Cusic et al. | |
| 2,687,414 A | 8/1954 | Cusic | |
| 3,142,678 A | 7/1964 | Rice et al. | |
| 3,329,571 A | 7/1967 | Rice et al. | |
| 5,494,928 A | 2/1996 | Bos | |
| 5,561,150 A | 10/1996 | Wichmann | |
| 5,633,276 A | 5/1997 | North et al. | |
| 5,646,173 A | 7/1997 | Bos et al. | |
| 5,755,829 A | 5/1998 | Terronova et al. | |
| 6,433,175 B1 | 8/2002 | Adams et al. | |
| 6,706,750 B1 | 3/2004 | Bentley et al. | |

FOREIGN PATENT DOCUMENTS

| | | |
|---|---|---|
| DE | 930 988 | 7/1955 |
| WO | WO 95/17405 A1 | 6/1995 |
| WO | WO 98/30548 A1 | 7/1998 |
| WO | WO98/56768 | 12/1998 |
| WO | WO 00/12475 A1 | 3/2000 |
| WO | WO 00/12502 A1 | 3/2000 |
| WO | WO 01/12603 | 2/2001 |

OTHER PUBLICATIONS

Curr. Opin. Invest. Drugs (Apr. 1993), 2(4):317-362.
European J. Pharmacol. 359 (1998), 33-40.
Int. J. Fertility and Women's Medicine 42(2) 67-72.

Primary Examiner—Joseph K. McKane
Assistant Examiner—Rebecca Anderson
(74) Attorney, Agent, or Firm—Foley & Lardner LLP

(57) ABSTRACT

A chemical compound of formula (I) wherein $R_1$ and $R_2$ are independently selected from hydrogen and alkyl; $R_3$ is alkyl; $R_4$ and $R_5$ are selected from hydrogen and alkyl; $R_6$ and $R_7$ are independently selected from hydrogen, halogen, hydroxyl, alkyl, aryl, amino, alkylamino, dialkylamino, alkoxy, aryloxy, alkylthio, alkylsulfoxyl, nitro, carbonitrile, carbo-alkoxy, carbo-aryloxy and carboxyl; and A is a 5- or 6-membered ring optionally containing one or more heteroatoms wherein the atoms of the ring A, other than the unsaturated carbon atoms of the phenyl ring to which the ring A is fused, are saturated or unsaturated, and pharmaceutically acceptable salts, addition compounds and prodrugs thereof; and the use thereof in therapy, particularly as an agonist or antagonist of a 5HT receptor, particularly a $5HT_{2C}$ receptor, for instance in the treatment of disorders of the central nervous system; damage to the central nervous system; cardiovascular disorders; gastrointestinal disorders; diabetes insipidus, and sleep apnea, and particularly for the treatment of obesity.

11 Claims, No Drawings

CONDENSED INDOLINE DERIVATIVES AND THEIR USE AS 5HT, IN PARTICULAR 5HT$_{2C}$, RECEPTOR LIGANDS

The present invention relates to indoline derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$, and obesity as a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin release/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, Psychopharmacol., 1988, 98, 93–100; G. A. Kennett, C. T. Dourish and G. Curzon, Eur. J. Pharmacol., 1987, 141, 429–453) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single injection of mCPP decreased food intake in female volunteers (A. E. S. Walsh et al., Psychopharmacol., 1994, 116, 120–122) and decreased the appetite and body weight of obese male and female subjects during subchronic treatment for a 14 day period (P. A. Sargeant et al., Psychopharmacol., 1997, 113, 309–312). The anorectic action of mCPP is absent in 5-HT$_{2C}$ receptor knockout mutant mice (L. H. Tecott et al., Nature, 1995, 374, 542–546) and is antagonised by the 5-HT$_{2C}$ receptor antagonist SB-242084 in rats (G. A. Kennett et al., Neuropharmacol., 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders. WO 9517405 discloses methods for the preparation of indolines for use as melatonin receptor ligands.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided a chemical compound of formula (I):

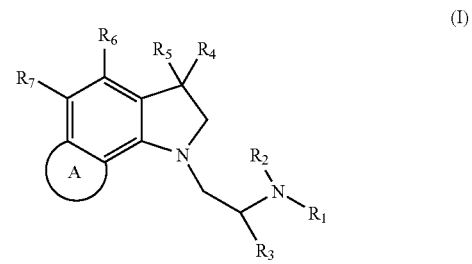

wherein:
R$_1$ and R$_2$ are independently selected from hydrogen and alkyl;
R$_3$ is alkyl;
R$_4$ and R$_5$ are selected from hydrogen and alkyl;
R$_6$ and R$_7$ are independently selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl; and
A is a 5 or 6-membered ring optionally containing one or more heteroatoms wherein the atoms of the ring A, other than the unsaturated carbon atoms of the phenyl ring to which the ring A is fused, are saturated or unsaturated, and pharmaceutically acceptable salts, addition compounds and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl, cycloalkenyl and cycloalkynyl.

As used herein, the term "lower alkyl" means a branched or unbranched, cyclic or acyclic, saturated or unsaturated (e.g. alkenyl or alkynyl) hydrocarbyl radical, wherein a cyclic lower alkyl group is $C_5$, $C_6$ or $C_7$, and wherein an acyclic lower alkyl group is methyl, ethyl, propyl (n-propyl or isopropyl) or butyl (n-butyl, isobutyl or tertiary-butyl), more preferably methyl.

As used herein, the term "aryl" means an aromatic group, such as phenyl or naphthyl, or a heteroaromatic group containing one or more heteroatom(s), such as pyridyl, pyrrolyl, quinolinyl, furanyl, thienyl, oxadiazolyl, thiadiazolyl, thiazolyl, oxazolyl, isoxazolyl, pyrazolyl, triazolyl, imidazolyl or pyrimidinyl.

As used herein, the term "alkoxy" means alkyl-O—. As used herein, the term "aryloxy" means aryl-O—.

As used herein, the term "halogen" means a fluorine, chlorine, bromine or iodine radical, preferably a fluorine or chlorine radical.

As used herein the term "prodrug" means any pharmaceutically acceptable prodrug of the compound of formula (I) which is metabolised in vivo to a compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, dichloroacetic, ethanesulfonic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids, and particularly fumaric acid. Acceptable base salts include alkali metal (e.g. sodium, potassium), alkaline earth metal (e.g. calcium, magnesium) and aluminium salts.

As used herein, the term "addition compound" means any pharmaceutically acceptable addition compound of the compound of formula (I). Addition compounds include those which are formed without change of valency from the union between a compound of formula (I) and one or more other molecules, particularly solvates, hydrates and inclusion complexes (such as cyclodextrin complexes).

As used herein, the term "A is a 5- or 6-membered ring" refers to a ring containing 5 or 6 ring atoms in total, i.e. including the carbon atoms in the unsaturated positions of the phenyl ring to which A is fused.

Where any of $R_1$ to $R_7$ is an alkyl group or an alkyl-containing group (such as alkoxy, alkylamino or alkylthio, for instance) as defined in formula (I) above, then that alkyl group, or the alkyl group of the alkyl-containing group, may be substituted or unsubstituted. Where either $R_6$ or $R_7$ is an aryl group or an aryl-containing group (such as aryloxy, for instance) as defined in formula (I), then said aryl group, or the aryl group of the aryl-containing group, may be substituted or unsubstituted. The ring A may be substituted or unsubstituted. Where any of $R_1$ to $R_7$ or A is substituted, there will generally be 1 to 3 substituents present, preferably 1 substituent. Substituents may include:

carbon-containing groups such as
  alkyl,
  aryl, (e.g. substituted and unsubstituted phenyl),
  arylalkyl; (e.g. substituted and unsubstituted benzyl);
halogen atoms and halogen containing groups such as
  haloalkyl (e.g. trifluoromethyl),
  haloaryl (e.g. chlorophenyl);
oxygen containing groups such as
  alcohols (e.g. hydroxy, hydroxyalkyl, hydroxyaryl, (aryl)(hydroxy)alkyl),
  ethers (e.g. alkoxy, aryloxy, alkoxyalkyl, aryloxyalkyl, alkoxyaryl, aryloxyaryl),
  aldehydes (e.g. carboxaldehyde),
  ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
  acids (e.g. carboxy, carboxyalkyl, carboxyaryl),
  acid derivatives such as esters (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl),
  amides (e.g. aminocarbonyl, mono- or di-alkylaminocarbonyl, aminocarbonylalkyl, mono- or di-alkylaminocarbonylalkyl, arylaminocarbonyl or arylalkylaminocarbonyl, alkylcarbonylamino, arylcarbonylamino or arylalkylcarbonylamino),
  carbamates (eg. alkoxycarbonylamino, aryloxycarbonylamino, arylalkyloxycarbonylamino, aminocarbonyloxy, mono- or di-alkylaminocarbonyloxy, arylaminocarbonyloxy or arylalkylaminocarbonyloxy)
  and ureas (eg. mono- or di-alkylaminocarbonylamino, arylaminocarbonylamino or arylalkylaminocarbonylamino);
nitrogen containing groups such as
  amines (e.g. amino, mono- or dialkylamino, arylamino, aminoalkyl, mono- or dialkylaminoalkyl),
  azides,
  nitriles (e.g. cyano, cyanoalkyl),
  nitro;
sulfur containing groups such as
  thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl)
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

In the compounds of formula (I), preferably $R_1$ and $R_2$ are independently selected from hydrogen and lower alkyl (preferably acyclic lower alkyl and more preferably methyl), and preferably from hydrogen. Where $R_1$ and $R_2$ are selected from alkyl, it is preferred that said alkyl groups are unsubstituted.

Preferably, the compounds of formula (I) are selected from compounds in which $R_1$ is the same as $R_2$. Preferably, $R_1$ and $R_2$ are both hydrogen.

The compounds of formula (I) are selected from compounds in which $R_3$ is alkyl, preferably lower alkyl, more preferably acyclic lower alkyl, and most preferably methyl.

$R_4$ and $R_5$ are independently selected from hydrogen and alkyl (including cycloalkyl, halo-alkyl (such as trifluoromethyl) and arylalkyl). Preferably $R_4$ and $R_5$ are independently selected from hydrogen and loweralkyl, more preferably from hydrogen and acyclic lower alkyl, and most preferably hydrogen.

$R_6$ and $R_7$ are preferably independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl. Preferably, $R_6$ and $R_7$ are independently selected from hydrogen and alkyl, more preferably from hydrogen and lower alkyl, more preferably from hydrogen and acyclic lower alkyl, and preferably from hydrogen.

It will be understood that the ring A may be a partially unsaturated ring (including a partially unsaturated heterocyclic ring) or an aromatic ring (including a heteroaromatic ring). As noted above, the ring A may be substituted or unsubstituted. Where substituted, the substituent group may be present on a carbon atom of the ring or, where the ring a contains one or more heteroatom(s) and where the valency of the heteroatom allows substitution, on a heteroatom of the ring.

As noted herein, the term "partially unsaturated ring" refers to a ring which contains unsaturated ring atoms and one or more double bonds but which is not aromatic, for example a cyclopentenyl or cyclohexenyl ring. It will be appreciated therefore that a partially unsaturated ring A may contain one double bond, i.e. the double bond between the unsaturated carbon atoms of the phenyl ring to which the ring A is fused, in which case the atoms of the ring A, other than the carbon atoms in the unsaturated positions of the phenyl ring to which A is fused, are saturated. Alternatively, a partially unsaturated ring A may contain an additional double bond provided that this additional double bond does not result in the ring A being aromatic.

Where A contains one or more heteroatom(s), it is preferred that the heteroatoms are selected from N, O and S. In one embodiment, the heteroatom(s) are selected from O and S. Where A contains one or more heteroatom(s), preferably A contains one or two heteroatom(s) and preferably only one heteroatom.

In one embodiment, where A contains heteroatom(s) then A is partially unsaturated. In a further embodiment, where A is aromatic then A contains no heteroatoms.

Preferably A is partially unsaturated.

It is preferred that A is a 5-membered ring, particularly a 5-membered partially unsaturated ring.

It is preferred that A is partially unsaturated, preferably wherein the atoms of the ring A, other than the unsaturated carbon atoms of the phenyl ring to which the ring A is fused, are saturated.

In one embodiment, the compounds of formula are selected from compounds wherein A is a 5-membered partially unsaturated carbocyclic ring or a 5-membered heterocyclic ring (preferably partially unsaturated), and preferably from compounds wherein A is a 5-membered partially unsaturated heterocyclic ring (preferably wherein the heteroatom(s) of the ring are O or S, particularly O).

In a further embodiment the compounds of formula (I) are selected from compounds wherein A is selected from the group consisting of cyclohexenyl, cyclopentenyl, phenyl, dihydrofuranyl, dihydropyranyl, dihydrothienyl, 2,3-dihydro-1,4-dioxin and tetrahydropyridinyl (including N-acetyltetrahydropyridinyl).

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, the preferred stereochemistry at the carbon atom to which $R_3$ and $NR_1R_2$ are bound is (S).

In one embodiment of the invention, the compounds are preferably selected from:
(S)-1-(benz[g]indolin-1-yl)-2-propylamine,
(R)-1-(benz[g]indolin-1-yl)-2-propylamine,
(S)-1-(2,3,7,8-tetrahydrofuro[2,3-g]indol-1-yl)-2-propylamine,
(S)-1-(2,3,7,8-tetrahydro-9H-pyrano[2,3-g]indol-1-yl)-2-propylamine,
(S)-1-(2,3,7,8-tetrahydrothieno[2,3-g]indol-1-yl)-2-propylamine,
(S)-1-(2,3,7,8-tetrahydro-9H-1,4-dioxino[2,3-g]indol-9-yl)-2-propylamine,
(S)-1-(2,3,6,7,8,9-hexahydro-1H-benz[g]indol-1-yl)]-2-propylamine,
(S)-1-[1-(1,2,3,6,7,8-hexahydrocyclopent[g]indolyl)]-2-propylamine,
[2S,3'(R or S)]-1-(3-ethyl-2,3,7,8-tetrahydrofuro[2,3-g]indol-1-yl)-2-propylamine,
[2S,3'(S or R)]-1-(3-Ethyl-2,3,7,8-tetrahydrofuro[2,3-g]indol-1-yl)-2-propylamine and
(S)-2-[6-(acetyl)-1-(2,3,6,7,8,9-hexahydro-pyrrolo[2,3-f]quinolinyl)]-2-propylamine.

In a preferred embodiment of the invention, the compounds are selected from:
(S)-1-(benz[g]indolin-1-yl)-2-propylamine,
(S)-1-(2,3,7,8-tetrahydrofuro[2,3-g]indol-1-yl)-2-propylamine,
(S)-1-(2,3,7,8-tetrahydrothieno[2,3-g]indol-1-yl)-2-propylamine,
(S)-1-(2,3,7,8-tetrahydro-9H-pyrano[2,3-g]indol-1-yl)-2-propylamine,
(S)-1-[1-(1,2,3,6,7,8-hexahydrocyclopent[g]indolyl)]-2-propylamine,
[2S,3(R or S)]-1-(3-ethyl-2,3,7,8-tetrahydrofuro[2,3-g]indol-1-yl)-2-propylamine and
[2S,3(S or R)]-1-(3-ethyl-2,3,7,8-tetrahydrofuro[2,3-g]indol-1-yl)-2-propylamine,
and more preferably from (S)-1-(2,3,7,8-tetrahydrofuro[2,3-g]indol-1-yl)-2-propylamine
and (S)-1-[1-(1,2,3,6,7,8-hexahydrocyclopent[g]indolyl)]-2-propylamine.

According to a further aspect of the invention, there is provided a compound of formula (I) for use in therapy.

The compounds of formula (I) may be used in the treatment (including prophylactic treatment) of disorders associated with 5-$HT_2$ receptor function. The compounds may act as receptor agonists or antagonists, preferably receptor agonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where 5-HT$_{2C}$ receptor activity is required, and preferably where a 5-HT$_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treating a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I), for instance in the manner described below in Reaction Scheme 1. $R_1$ to $R_7$ are as previously defined.

The N-alkylindole (III) may be formed by reaction of the indole (II) with an appropriate carbamylethylsulfonate in the presence of a strong base such as potassium hydroxide in a solvent such as methyl sulfoxide. Where required, the N-alkylindole (IV) may be obtained from the N-alkylindole (III) by reaction with an acylating agent eg. acetic anhydride in the presence of an acid catalyst followed by treatment with a reducing agent eg. diborane in a solvent such as THF. The indoline (V) may be obtained via reduction of the N-alkylindole (IV) with a reducing agent such as sodium cyanoborohydride or tetrabutylammonium borohydride in a solvent such as acetic acid or dichloromethane. The indoline (I) ($R_1=R_2=H$) may be obtained by reaction of the indoline (V) with a reagent suitable to reveal the protected amine function.

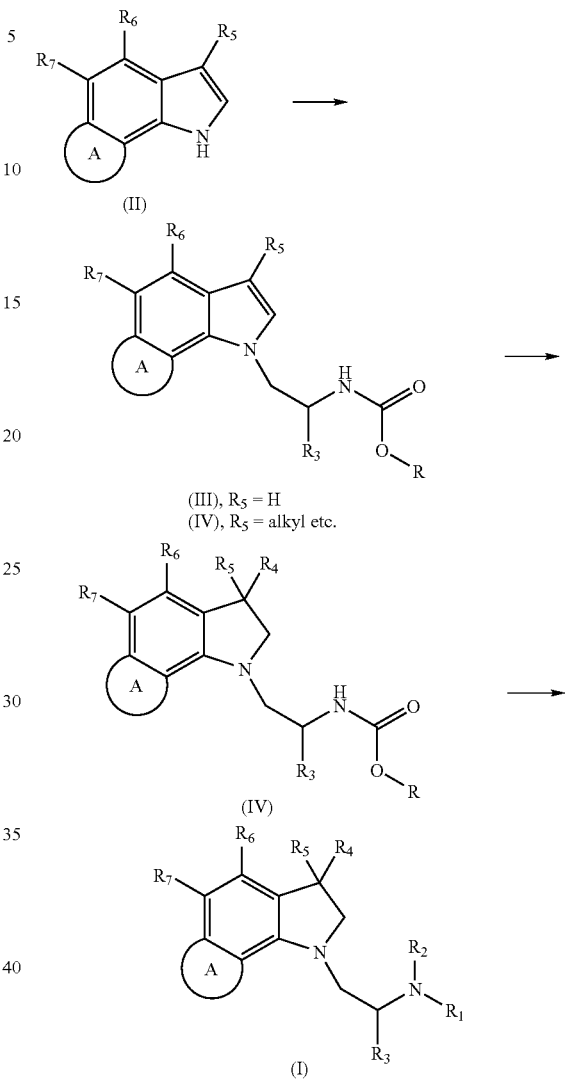

Reaction Scheme 1

(II)

(III), $R_5 = H$
(IV), $R_5 =$ alkyl etc.

(V)

(I)

The compounds of formula (I) ($R_1$ and/or $R_2$=alkyl) may be prepared from compounds of formula (I) ($R_1=R_2=H$) by standard methods such as reductive alkylation with an appropriate aldehyde or ketone in the presence of a reducing agent such as sodium triacetoxyborohydride, formic acid or sodium cyanoborohydride.

If, in any of the other processes mentioned herein, any of the substituent groups $R_1$ to $R_7$ is other than the one required, the substituent group may be converted to the desired substituent by known methods. The substituents $R_1$ to $R_7$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilising and/or dispersing agents.

Alternatively, the active ingredient may be in a powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-$HT_{2C}$ receptor the 5-$HT_{2C}$ receptors were radiolabeled with [$^3$H]-5-HT. The affinity of the compounds for 5-$HT_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-$HT_{2B}$ receptor the 5-$HT_{2B}$ receptors were radiolabeled with [$^3$H]-5-HT. The affinity of the compounds for human 5-$HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-$HT_{2A}$ receptor the 5-$HT_{2A}$ receptors were radiolabeled with [$^{125}$I]-DOI. The affinity of the compounds for 5-$HT_{2A}$ receptors in a CHO cell line was determined according to the procedure of D. J. McKenna and S. J. Peroutka, *J. Neurosci.*, 1989, 9/10, 3482–90.

The thus-determined activity of compounds of formula (I) is shown in Table 1.

TABLE 1

| Compound | $K_i$ (2C) | $K_i$ (2B) | $K_i$ (2A) |
|---|---|---|---|
| 1 | 107 | 39 | 173 |
| 6 | 70 | 218 | 223 |

2. Functional Activity

The functional activity of compounds of formula (I) was assayed using a Fluorimetric Imaging Plate reader (FLIPR) in the following manner.

CHO cells expressing either the h5-$HT_{2C}$ or h5-$HT_{2A}$ receptors were counted and plated into standard 96 well microtitre plates before the day of testing to give a confluent monolayer. The following day the cells were dye loaded with the calcium sensitive dye Fluo 3-AM by incubation with serum free culture maintenance media containing pluronic acid and Fluo 3-AM dissolved in DMSO at 37° C. in a $CO_2$ incubator at 95% humidity for approximately 90 minutes. Unincorporated dye was removed by washing with Hanks balanced salt solution containing 20 mM HEPES and 2.5 mM probenecid (the assay buffer) using an automated cell washer to leave a total volume of 100 µl/well.

The drug (dissolved in 50 µl of assay buffer) was added at a rate of 70 µl/sec to each well of the FLIPR 96 well plate during fluorescence measurements. The measurements are taken at 1 sec intervals and the maximum fluorescent signal was measured (approx 10–15 secs after drug addition) and compared with the response produced by 10 µM 5-HT (defined as 100%) to which it is expressed as a percentage response (relative efficacy). Dose response curves were constructed using Graphpad Prism (Graph Software Inc.).

The thus determined activities of the compounds of formula (I) is shown in Table. 2.

TABLE 2

| Compound | h5-HT$_{2A}$ | | b5-HT$_{2c}$ | |
|---|---|---|---|---|
| | EC$_{50}$ (nM) | Relative Efficacy (%) | EC$_{50}$ (nM) | Relative Efficacy (%) |
| 1 | 1374 | 51 | 158 | 79 |
| 2 | >10000 | – | 1720 | 44 |
| 3 | 138 | 81 | 6 | 94 |
| 4 | 505 | 66 | 47 | 89 |
| 5 | 48 | 77 | 0.4 | 86 |
| 6 | 312 | 71 | 47 | 90 |
| 7 | 1835 | 14 | 440 | 68 |
| 8 | 10000 | 0 | 217 | 69 |
| 9 | 1143 | 22 | 50 | 74 |
| 10 | 403 | 15 | 51 | 67 |

SYNTHETIC EXAMPLES

Example 1

(S)-1-(Benz[g]indolin-1-yl)-2-propylamine Hemifumarate

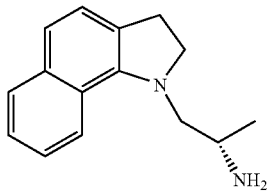

(S)-1-[2-(tert-Butoxycarbonylamino)propyl]-benz[g]indole

Benz[g]indole (1.5 g, 10 mmol) (Bartoli et al., *Tetrahedron Lett.*, 1989, 30(16), 2129–32) was added portionwise to a stirred suspension of powdered potassium hydroxide (85%, 4.8 g, 72 mmol) in methyl sulfoxide (50 mL). The mixture was warmed to 35° C. and stirred for 30 min. A solution of (S)-2-(tert-butoxycarbonylamino)propane methanesulfonate (11.4 g, 45 mmol) in methyl sulfoxide (20 mL) was added over 2 h. The mixture was stirred for 20 h and partitioned between water (100 mL) and ether (3×50 mL). The combined organic extracts were washed with brine (2×), dried (magnesium sulfate), concentrated in vacuo and purified by column chromatography [SiO$_2$; heptane-ethyl acetate (3:1)] to give the product (0.7 g, 12%) as a white solid: IR $\nu_{max}$ (Nujol)/cm$^{-1}$ 1686, 1529, 1366, 1176, 1058, 804 and 685; NMR $\delta_H$ (400 MHz, CDCl$_3$) 1.19 (3H, d, J 5.5 Hz), 1.54 (9H, s), 3.96–4.05 (1H, m), 4.36–4.51 (2H, m), 4.91 (1H, brs), 6.59 (1H, t, J 3 Hz), 7.04 (1H, d, J 3 Hz), 7.39 (1H, d, J 8 Hz), 7.48 (1H, d, J 8 Hz), 7.55 (1H, t, J 7 Hz) 7.66 (1H, d, J 8.5 Hz), 7.92 (1H, d, J 8.5 Hz) and 8.51 (1H, brs).

(S)-1-[2-(tert-Butoxycarbonylamino)propyl]-benz[g]indoline

To a stirred solution of (S)-1-[2-(tert-butoxycarbonylamino)propyl]-benz[g]indole (0.49 g, 1.5 mmol) in acetic acid (10 mL) was added portionwise sodium cyanoborohydride (95%, 0.30 g, 4.5 mmol). The mixture was stirred for 16 h and partitioned between ether (40 mL) and saturated aqueous sodium bicarbonate solution (3×50 mL). The organic layer was washed with brine (2×), dried (magnesium sulfate), concentrated in vacuo and purified by column chromatography [SiO$_2$; heptane-ethyl acetate (6:1)] to give the product (0.24 g, 49%) as a pale yellow solid: IR $\nu_{max}$ (Nujol)/cm$^{-1}$ 1689, 1528, 1362, 1298, 1051 and 790; NMR $\delta_H$ (400 MHz, CDCl$_3$) 1.39 (3H, d, J 6.5 Hz), 1.45 (9H, s), 3.11–3.28 (2H, m), 3.32–3.42 (2H, m), 3.62–3.69 (2H, m), 3.98–4.08 (1H, m), 4.78 (1H, brs), 7.30–7.38 (1H, m), 7.33–7.41 (3H, m), 7.72–7.81 (1H, m) and 7.98–8.01 (1H, m).

(S)-1-(Benz[g]indolin-1-yl)-2-propylamine Hemi-fumarate

To a stirred solution of (S)-1-[2-(tert-butoxycarbonylamino)propyl]-benz[g]indole (0.23 g, 0.7 mmol) in dichloromethane (2 mL) was added dropwise trifluoroacetic acid (2 mL). The mixture was stirred for 1 h and partitioned between aqueous sodium hydroxide solution (2 M, 20 mL) and dichloromethane (3×20 mL). The combined organic extracts were washed with brine (2×), dried (magnesium sulfate) and concentrated in vacuo to give a pale yellow oil. The oil was dissolved in 2-propanol (5 mL) and the solution was heated to boiling then fumaric acid (0.08 g, 0.7 mmol) was added. The mixture was cooled to 0° C. and filtered. The filter-cake was dried in vacuo to give the product (0.13 g, 65%) as a while solid: mp. 205–207° C.; NMR $\delta_H$ (400 MHz, DMSO-d$_6$) 1.23 (3H, d, J 6.5 Hz), 3.01–3.69 (7H, m), 6.39 (1H, s), 7.31–7.40 (4H, m), 7.83 (1H, m) and 8.06 (1H, m).

Example 2

(R)-1-(Benz[g]indolin-1-yl)-2-propylamine Hemifumarate

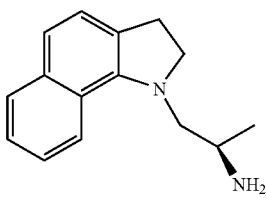

(R)-1-[2-(tert-Butoxycarbonylamino)propyl]-benz[g]indole (R)-1-[2-(tert-Butoxycarbonylamino)propyl]-benz[g]indole was prepared according to the method described in Example 1 using benz[g]indole and (R)-2-(tert-butoxycarbonylamino)propane methanesulfonate to give the product (0.69 g, 35%) as a pale yellow solid: IR $v_{max}$ (Nujol)/cm$^{-1}$ 1686, 1529, 1467, 1176, 1058, 804 and 722; NMR $\delta_H$ (400 MHz, CDCl$_3$) 1.15 (3H, d, J 7 Hz), 1.41 (9H, s), 4.16–4.28 (1H, m), 4.38–4.49 (2H, m), 4.91 (1H, brs), 6.59 (1H, d, J 3 Hz), 7.04 (1H, d, J 3 Hz), 7.40 (1H, t, J 7 Hz), 7.49 (1H, d, J 8.5 Hz), 7.55 (1H, t, J 7 Hz), 7.68 (1H, d, J 9 Hz), 7.91 (1H, d, J 8 Hz) and 8.50 (1H, brs).

(R)-1-[2-(tert-Butoxycarbonylamino)propyl]-benz[g]indoline (R)-1-[2-(tert-Butoxycarbonylamino)propyl]-benz[g]indoline was prepared according to the method described in Example 1 from (R)-1-[2-(tert-butoxycarbonylamino)propyl]benz[g]indole to give the product (0.14 g, 28%) as a pale yellow solid: IR $v_{max}$ (Nujol)/cm$^{-1}$ 1689, 1528, 1362, 1298, 1169, 1051 and 789; NMR $\delta_H$ (400 MHz, CDCl$_3$) 1.34 (3H, d, J 7.5 Hz), 1.41 (9H, s), 3.07–3.23 (2H, m), 3.27–3.35 (2H, m), 3.56–3.62 (2H, m), 3.95–4.03 (1H, m), 4.72 (1H, brs), 7.21–7.24 (1H, m), 7.28–7.35 (3H, m), 7.72 (1H, d, J 7.5 Hz) and 7.93 (1H, d, J 7.5 Hz).

(R)-1-(6-(Benz[g]indolin-1-yl)-2-propylamine Hemi-fumarate (R)-1-(6-(Benz[g]indolin-1-yl)-2-propylamine hemi-fumarate was prepared according to the method described in Example 1 using (R)-1-[2-(tert-butoxycarbonylamino)propyl]benz[g]indoline to give the product (0.12 g, 95%) as a white solid: mp. 205–207° C.; NMR $\delta_H$ (400 MHz, DMSO-d$_6$) 1.24 (3H, d, J 6.5 Hz), 3.01–3.69 (7H, m), 6.39 (1H, s), 7.31–7.40 (4H, m), 7.83 (1H, m) and 8.06 (1H, m).

Example 3

(S)-1-(2,3,7,8-Tetrahydrofuro[2,3-g]indol-1-yl)-2-propylamine Fumarate

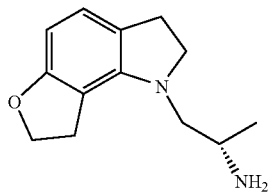

2,3-Dihydrobenzo[b]furan-5-carboxaldehyde and 2,3-dihydrobenzo[b]furan-7-carboxaldehyde To a stirred solution of 2,3-dihydrobenzo[b]furan (9.4 mL, 83.4 mmol) in dichloromethane (250 mL) under Ar at −5° C. was added dropwise titanium(IV) chloride (18 mL, 167.0 mmol) over 15 min, maintaining the temperature below 0° C. After addition was complete, the red-brown reaction mixture was allowed to stir for a further 10 min before α,α-dichloromethyl methyl ether (8.3 mL, 91.6 mmol) was added dropwise [CAUTION—exotherm] maintaining the temperature below 0° C. Upon complete addition, the vivid crimson reaction mixture was allowed to warm to ambient temperature over 2 h, and was then cautiously poured onto a saturated aqueous solution of sodium bicarbonate (700 mL). The mixture was filtered through a pad of Kieselguhr, which was washed through with dichloromethane. The phases were separated and the aqueous phase was extracted with dichloromethane (2×400 mL). The combined organic fractions were washed with brine (300 mL), dried (magnesium sulfate) and concentrated in vacuo to afford a mixture [5-CHO:7-CHO (4:1)] of aldehyde products (11.48 g, 93%) as a green-black liquid which was used without further purification.

Methyl 2-azido-3-(2,3-dihydrobenzo[b]furan-5-yl)propenate and Methyl 2-azido-3-(2,3-dihydrobenzo[b]furan-7-yl)propenate To a stirred solution of potassium tert-butoxide (31.0 g, 0.26 mol) in anhydrous methanol (220 mL) under Ar at −13° C. was added dropwise a mixture of methyl azidoacetate (31.7 g, 0.27 mol), and 2,3-dihydrobenzo[b]furan-5-carboxaldehyde and 2,3-dihydrobenzo[b]furan-7-carboxaldehyde (4:1 mixture; 10.15 g, 69 mmol) over 40 min. After complete addition, the reaction mixture was stirred at −10° C. for 1 h, then stored at 0° C. overnight (with a vent needle in place). The reaction mixture was partitioned between ethyl acetate (750 mL) and water (1 L) and the aqueous phase was extracted with ethyl acetate (2×300 mL). The combined organic fractions were washed with brine (300 mL), dried (magnesium sulfate) and concentrated in vacuo to afford a crude oil. Purification by flash column chromatography [SiO$_2$; dichloromethane-heptane (1:1)] afforded a mixture [5-substituted:7-substituted (4:1)] of products (11.4 g, 68%) as a pale yellow solid which was used without further purification.

Methyl 7,8-dihydrofuro[2,3-g]indole-2-carboxylate, Methyl 5,6-dihydrofuro[3,2-f]indole-2-carboxylate and Methyl 5,6-dihydrofuro[2,3-e]indole-2-carboxylate To stirred xylenes (800 mL) under Ar at reflux was added dropwise a solution of methyl 2-azido-3-(2,3-dihydrobenzo[b]furan-5-yl)propenate and methyl 2-azido-3-(2,3-dihydrobenzo[b]furan-7-yl)propenate (4:1 mixture; 11.4 g, 46.5 mmol) in xylenes (300 mL) over 3.5 h. After complete addition, the mixture was heated at reflux for a further 30 min, followed by removal of xylenes (750 mL) by distillation. The residual solution was allowed to cool, with stirring, to ambient temperature overnight. The resultant precipitate was filtered and washed with cold xylenes to afford a mixture [(2,3-g):(3,2-f)—1:1] of products (5.90 g, 59%) as a white solid which was used without further purification. The filtrate was concentrated in vacuo and the residue was recrystallised from hot xylenes (100 mL) to afford a mixture [(2,3-g):(3,2-f):(2,3-e)—12:48:40] of products (2.23 g, 22%) as a pale yellow solid.

7,8-Dihydrofuro[2,3-g]indole-2-carboxylic Acid and 5,6-dihydrofuro[3,2-f]indole-2-carboxylic Acid To a stirred suspension of methyl 7,8-dihydrofuro[2,3-g]indole-2-carboxylate and methyl 5,6-dihydrofuro[3,2-f]indole-2-carboxylate (1:1) (5.85 g, 26.9 mmol) in water (140 mL) was added potassium hydroxide (85%; 3.55 g, 53.8 mmol) and the mixture was heated at reflux for 3.75 h, then allowed to cool to ambient temperature. Hydrochloric acid (2.5N aqueous; 29 mL) was added and the resultant precipitate was filtered and washed with water to afford a mixture [(2,3-g):(3,2-f) 1:1] of products (5.47 g, 100%) as an off-white solid which was used without further purification.

7,8-Dihydrofuro[2,3-g]indole and 5,6-dihydrofuro[3,2-f]indole

A stirred solution of 7,8-dihydrofuro[2,3-g]indole-2-carboxylic acid and 5,6-dihydrofuro[3,2-f]indole-2-carboxylic acid (1:1) (5.46 g, 26.9 mmol) in phenyl ether (250 mL) was heated at reflux for 45 min, then allowed to cool to ambient temperature. Heptane (500 mL) was added and the mixture was passed through a heptane-packed SiO$_2$ column under pressure. The column was eluted with heptane (1.5 L), then heptane-dichloromethane (1:1, 1L) and finally dichloromethane to afford 7,8-dihydrofuro[2,3-g]indole (230 mg, 5.4%) as a white solid. IR $v_{max}$ (Nujol)/cm$^{-1}$ 3382, 2925, 2854, 1644, 1618, 1497, 1463, 1441, 1435, 1368, 1326, 1234, 1140, 1021, 970, 793, 719, 622, 533 and 475; NMR (400 MHz, CDCl$_3$) $\delta_H$ 3.31 (2H, t, J 8.5 Hz), 4.66 (2H, t, J 8.5 Hz), 6.51 (1H, dd, J 2, 3.5 Hz), 6.73 (1H, d, J 8 Hz), 7.06 (1H, dd, J 2, 3.5 Hz), 7.39 (1H, d, J 8.5 Hz) and 7.83 (1H, brs). Also collected were 5,6-dihydrofuro[3,2-f]indole (667 mg, 15.6%) and mixed fractions (2.94 g, 68.7%). The mixed isomers were further separated by flash column chromatography [SiO$_2$; ethyl acetate-heptane (1:3)] to afford afford 7,8-dihydrofuro[2,3-g]indole (408 mg, 9.5%) as a white solid and 5,6-dihydrofuro[3,2-f]indole (690 mg, 16%).

(S)-1-[2-(tert-Butoxycarbonylamino)propyl]-7,8-dihydrofuro[2,3-g]indole

To a stirred solution of 7,8-dihydrofuro[2,3-g]indole (392 mg, 2.46 mmol) in dimethyl sulfoxide under Ar at 38° C. (external temperature) was added powdered potassium hydroxide (85%; 650 mg, 9.85 mmol) and the resultant suspension was stirred for 1 h. A solution of (S)-2-(tert-butoxycarbonylamino)propane methanesulfonate (1.50 g, 5.9 mmol) was added dropwise over 45 min, and the mixture was stirred for 4 days. After this time, the reaction was quenched by pouring onto ice-water (100 mL), the resultant suspension was filtered and the solid was washed with ice-cold water to afford the product (580 mg, 74%) as a pale pink solid. R$_f$ 0.25 [Ethyl acetate-heptane (3:7)]; IR $v_{max}$ (Nujol)/cm$^{-1}$ 3360, 2925, 2854, 1687, 1516, 1460, 1366, 1341, 1299, 1233, 1224, 1173, 1079, 969, 794, 712 and 608; NMR (400 MHz, CDCl$_3$) $\delta_H$ 1.09 (3H, d, J 6.5 Hz), 1.39 (9H, s), 3.52 (1H, m), 3.59 (1H, m), 3.99 (2H, m), 4.27 (1H, m), 4.63 (2H, t, J 9 Hz), 6.42 (1H, d, J 3.5 Hz), 6.68 (J, d, J 8.5 Hz), 6.89 (1H, d, J 3.5 Hz) and 7.33 (1H, d, J 8.5 Hz).

(S)-1-[2-(tert-Butoxycarbonylamino)propyl]-2,3,7,8-tetrahydrofuro[2,3-g]indole

To a stirred solution/suspension of (S)-1-[2-(tert-butoxycarbonylamino)propyl]-7,8-dihydrofuro[2,3-g]indole (565 mg, 1.79 mmol) in acetic acid (40 mL) under Ar at 5° C. was added sodium cyanoborohydride (371 mg, 5.90 mmol) and the mixture was allowed to warm to ambient temperature and stir overnight. The resultant solution was poured onto ice-water (100 mL), basified (~pH 8–9) by the addition of 30% ammonium hydroxide, and the resultant suspension was filtered and the solid washed with ice-cold water. The crude solid was purified by flash column chromatography [SiO$_2$; ethyl acetate-heptane (3:7)] to afford the product (412 mg, 72%) as a white solid: mp 141–142.5° C.; Found: C, 67.87; H, 8.21; N, 8.80%. C$_{18}$H$_{26}$N$_2$O$_3$ requires: C, 67.90; H, 8.23; N, 8.79%.

(S)-1-(2,3,7,8-Tetrahydrofuro[2,3-g]indol-1-yl)-2-propylamine Fumarate

To a stirred solution/suspension of (S)-1-[2-(tert-butoxycarbonylamino)propyl]-2,3,7,8-tetrahydrofuro[2,3-g]indole (392 mg, 1.23 mmol) in methanol (25 mL) was added conc. hydrochloric acid (0.37 mL) and the mixture was heated at reflux for 1.5 h, then allowed to cool to ambient temperature. The solvent was removed in vacuo and the residue was triturated with ether and a small amount of acetone, filtered, and washed with ether to afford the product (366 mg, 100%) as the bis-hydrochloride salt. 326 mg of this salt was partitioned between ether and aqueous sodium hydroxide solution, and the aqueous phase was extracted with ether. The combined organic fractions were dried (magnesium sulfate) and concentrated in vacuo to afford the free amine as a pale yellow oil (216 mg). A solution of the above oil in hot 2-propanol (0.5 mL) was added to a stirred solution of fumaric acid (127 mg, 1.09 mmol) in hot 2-propanol (2 mL), and the resultant suspension was allowed to cool to ambient temperature and was then cooled to 0° C. The solid was filtered and washed with ice-cold 2-propanol, followed by ether to afford the product (279 mg, 76%) as a white solid: mp. 215.5–217° C. (dec.); Found: C, 60.98; H, 6.78; N, 8.26%. C$_{13}$H$_{18}$N$_2$O.C$_4$H$_4$O$_4$ requires: C, 61.07; H, 6.63; N, 8.37%.

Alternatively Example 3 may be synthesised using the following procedure.

2-(2'-Hydroxyethyl)-3-methoxy-N-tert-butoxycarbonylaniline

A stirred solution of N-tert-butoxycarbonyl-anisidine (431 g, 1.93 mol) in ether (2 L) under an argon atmosphere was cooled to −20° C. A solution of tert-butyllithium (1.7 M, hexanes, 2.5 L, 4.25 mol) was added dropwise and the reaction was stirred for 3 h at −20° C. The reaction was cooled to −50° C. and ethylene oxide (136 g, 3.09 mol) was added dropwise. The reaction was warmed to 0° C. over 1 h and then stirred at room temperature for 1 h. The reaction was poured onto saturated aqueous ammonium chloride solution (2.5 L) and the mixture was extracted with ether (3×2.5 L). The organic extracts were combined and concentrated in vacuo to afford a pale yellow oil which was purified by column chromatography [SiO$_2$; heptane-ethyl acetate (5:1)] to afford the title compound (176 g, 37%) as a yellow crystalline solid; NMR (400 MHz, CDCl$_3$) $\delta_H$ 1.51 (9H, br s), 2.91 (2H, t, J 6.0 Hz), 3.79 (3H, s), 3.87 (2H, q, J 5.0 Hz, 10.5 Hz), 6.64 (1H, d, J 8.0 Hz), 7.18 (1H, t, J 9.0 Hz), 7.38 (1H, m), 7.55 (1H, br s); IR $v_{max}$ (Nujol)/cm$^{-1}$ 3407, 3212, 2955, 2854, 1721, 1592, 1508, 1476, 1438, 1370, 1267, 1234, 1162, 1047 and 773.

2,3-Dihydro-4-benzofuranamine 2-(2'-Hydroxyethyl)-3-methoxy-N-tert-butoxycarbonylaniline (158 g, 0.59 mol) was added portionwise to a stirred solution of hydrogen bromide in acetic acid (30%, 1.7 L) at room temperature. The reaction was then heated to reflux for 4 h. The reaction mixture was cooled to room temperature, basified to pH 14 with aqueous sodium hydroxide solution (6 N) and extracted with dichloromethane (3×2 L). The organic extracts were combined, dried (magnesium sulphate) and evaporated to give the title compound as an orange oil (78 g, 92%); NMR (400 MHz, CDCl$_3$) $\delta_H$ 2.99 (2H, t, J 8.5 Hz), 3.55 (2H, br s), 4.57 (2H, t, J 8.5 Hz), 6.19 (1H, d, J 7.5 Hz), 6.25 (2H, d, J 7.5 Hz), 6.92 (1H, t, J 8.0 Hz); IR $v_{max}$ (Nujol)/cm$^{-1}$ 2853, 2610, 1544, 1462, 1262, 1234, 986 and 761.

N-[5-(2,3-Dihydrobenzo[b]furanyl)]-2-(hydroxyimino)acetamide

A mixture of 2,3-dihydro-4-benzofuranamine (72.3 g, 0.54 mol), hydroxylamine hydrochloride (131.3 g, 1.8 mol), conc. hydrochloric acid (45 mL) and water (1265 mL) was stirred at room temperature for 30 min. A solution of chloral hydrate (98.2 g, 0.59 mol) in water (1265 mL) was added followed by solid sodium sulphate (767 g, 5.4 mol) and the reaction was heated to reflux for 1 h. The reaction was cooled to room temperature and the solid was collected by filtration. The solid was suspended in ethyl acetate (250 mL) and water (250 mL) and then extracted with ethyl acetate (3×250 mL). The organic extracts were combined, dried (magnesium sulphate) and concentrated in vacuo to afford the title compound (41 g, 38%) as a pale brown solid; NMR (400 MHz, DMSO-d$_6$) $\delta_H$ 3.12 (2H, t, J 9.0 Hz), 4.52 (2H, t, J 8.5 Hz), 6.58 (1H, d, J 8.0 Hz), 7.06 (1H, t, J 8.5 Hz), 7.14 (1H, d, J 8.5 Hz), 7.7 (1H, s), 9.66 (1H, br s), 12.19 (1H, br s); IR $v_{max}$ (Nujol)/cm$^{-1}$ 3389, 3160, 2923, 1661, 1620, 1607, 1540, 1453., 1238, 1060, 1029, 982 and 780.

2,3,7,8-Tetrahydro-1H-furo[2,3-g]indole-2,3-dione

Methanesulfonic acid (200 mL) was added to N-[5-(2,3-dihydrobenzo[b]furanyl)]-2-(hydroxyimino)acetamide (17 g, 82.5 mmol) with vigorous stirring at 0° C. The mixture was stirred at 0° C. for 1 h then poured onto ice-water (500 mL). The aqueous mixture was neutralised (ammonium hydroxide) and filtered to afford the title compound (12.4 g, 80%) as a red solid; NMR (400 MHz, DMSO-$d_6$) $\delta_H$ 3.08 (2H, t, J 8.5 Hz), 4.72 (2H, t, J 8.5 Hz), 6.45 (1H, d, J 8.0 Hz), 7.37 (1H, d, J 8.0 Hz), 11.15 (1H, br s); IR $\nu_{max}$ (Nujol)/cm$^{-1}$ 3225, 2925, 1752, 1709, 1642, 1605, 1490, 1448, 1377, 1357, 1243 and 1039.

7,8-Dihydro-1H-furo[2,3-g]indole

A solution of 2,3,7,8-tetrahydro-1H-furo[2,3-g]indole-2,3-dione (9.05 g, 47.9 mmol) in tetrahydrofuran (100 mL) was stirred at −20° C. under an argon atmosphere. Solid sodium borohydride was added portionwise and the reaction was stirred for 20 min at −20° C. Boron trifluoride etherate (11.9 mL, 96 mmol) was added dropwise over 90 min, then the mixture was warmed to 0° C. and stirred for 1 h. The reaction was quenched with water (100 mL) and the solution was extracted with ethyl acetate (3×150 mL). The organic extracts were combined, dried (magnesium sulphate) and concentrated in vacuo to afford a yellow solid which was purified by column chromatography [SiO$_2$; heptane-ethyl acetate (5:1)] to afford the title compound (3.2 g, 42.8%); analytical data as described above.

The synthesis of Example 3 was completed as described above.

Example 4

(S)-1-(2,3,7,8-Tetrahydro-9H-pyrano[2,3-g]indol-1-yl)-2-propylamine Fumarate

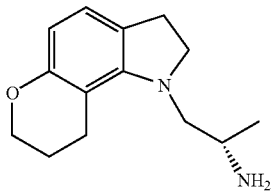

Chroman

To a stirred solution of 4-hydroxychroman (10.14 g, 67.5 mmol) in acetic acid (150 mL) under Ar was added acetic anhydride (12.7 mL, 135 mmol) and the mixture was heated at reflux for 3 h, then allowed to cool to ambient temperature. Palladium on carbon (10 wt %; 1.8 g, 2.5 mol %) was added and the mixture was shaken in a Parr hydrogenator under a 42 psi atmosphere of hydrogen overnight. The reaction mixture was filtered, the solvent was removed in vacuo and the residue was taken-up in ethyl acetate. The solution was washed with saturated aqueous sodium bicarbonate solution, brine, dried (magnesium sulfate) and concentrated in vacuo to afford the product (7.73 g, 85%) as a pale yellow liquid: IR $\nu_{max}$ (film)/cm$^{-1}$ 2937, 2863, 1737, 1609, 1582, 1490, 1456, 1304, 1267, 1228, 1189, 1116, 1065, 1008 and 754; NMR (400 MHz, CDCl$_3$) $\delta_H$ 2.00 (2H, m), 2.78 (2H, t, J 6.5 Hz), 4.17 (2H, t, J 7 Hz), 6.81 (2H, m) and 7.05 (2H, m).

Chroman-6-carboxaldehyde and chroman-8-carboxaldehyde

A mixture of chroman-6-carboxaldehyde and chroman-8-carboxaldehyde was prepared according to the method described in Example 3, using chroman (7.70 g, 57.4 mmol) to produce a mixture [6-CHO:8-CHO (1:1)] of aldehyde products (8.98 g, 96%) as a pale orange liquid which was used without further purification.

Methyl 2-azido-3-(2,3-dihydro-4H-benzopyran-6-yl)propenate and Methyl 2-azido-3-(2,3-dihydro-4H-benzopyran-8-yl)propenate Methyl 2-azido-3-(2,3-dihydro-4H-benzopyran-6-yl)propenate and methyl 2-azido-3-(2,3-dihydro-4H-benzopyran-8-yl)propenate were prepared according to the method described in Example 3, using a mixture (1:1) of chroman-6-carboxaldehyde and chroman-8-carboxaldehyde (8.95 g, 55.2 mmol) to produce after purification by flash column chromatography [SiO$_2$; dichloromethane-heptane (1:1)] a mixture [6-substituted:8-substituted (3:1)] of products (5.15 g, 36%) as a pale yellow solid which was used without further purification.

Methyl 7,8-dihydro-9H-pyrano[2,3-g]indole-2-carboxylate, Methyl 6,7-dihydro-5H-pyrano[3,2-f]indole-2-carboxylate and Methyl 5,6-dihydro-7H-pyrano[2,3-e]indole-2-carboxylate Methyl 7,8-dihydro-9H-pyrano[2,3-g]indole-2-carboxylate, methyl 6,7-dihydro-5H-pyrano[3,2-f]indole-2-carboxylate and methyl 5,6-dihydro-7H-pyrano[2,3-e]indole-2-carboxylate were prepared according to the method described in Example 3, using a mixture (3:1) of methyl 2-azido-3-(2,3-dihydro-4H-benzopyran-6-yl)propenate and methyl 2-azido-3-(2,3-dihydro-4H-benzofuran-8-yl)propenate (5.1 g, 19.7 mmol) to produce a mixture [(2,3-g):(3,2-f):(2,3-e)—10:2:5] of products (4.33 g, 94%) as a yellow solid which was used without further purification.

7,8-Dihydro-9H-pyrano[2,3-g]indole-2-carboxylic Acid, 6,7-dihydro-5H-pyrano[3,2-f]indole-2-carboxylic Acid and 5,6-dihydro-7H-pyrano[2,3-e]indole-2-carboxylic Acid 7,8-Dihydro-9H-pyrano[2,3-g]indole-2-carboxylic acid, 6,7-dihydro-5H-pyrano[3,2-f]indole-2-carboxylic acid and 5,6-dihydro-7H-pyrano[2,3-e]indole-2-carboxylic acid were prepared according to the method described in Example 3, using a mixture (10:5:2) of methyl 7,8-dihydro-9H-pyrano[2,3-g]indole -2-carboxylate, methyl 6,7-dihydro-5H-pyrano[3,2-f]indole -2-carboxylate and methyl 5,6-dihydro-7H-pyrano[2,3-e]indole -2-carboxylate (4.33 g, 18.7 mmol) to produce, after trituration with isopropyl ether, a mixture [(2,3-g):(3,2-f):(2,3-e)—7:1:2] of products (2.30 g, 57%) as a white solid. The filtrate was evaporated and purified by flash column chromatography [SiO$_2$; ethyl acetate-heptane (2:1)+0.5% acetic acid] to afford an oil which solidified upon treatment with isopropyl ether-heptane to afford a mixture [(2,3-g):(3,2-f):(2,3-e)—44:22:34] of products (818 mg, 20%) as a white solid. The products were combined and used without further purification.

7,8-Dihydro-9H-pyrano[2,3-g]indole, 6,7-dihydro-5H-pyrano[3,2-g]indole and 5,6-dihydro-7H-pyrano[2,3-e]indole 7,8-Dihydro-9H-pyrano[2,3-g]indole, 6,7-dihydro-5H-pyrano[3,2-g]indole and 5,6-dihydro-7H-pyrano[2,3-e]indole were prepared according to the procedure described in Example 3, using a mixture [(2,3-g):(3,2-f):(2,3-e)—11:1:4] of 7,8-dihydro-9H-pyrano[2,3-g]indole-2-carboxylic acid, 6,7-dihydro-5H-pyrano[3,2-f]indole-2-carboxylic acid and 5,6-dihydro-7H-pyrano[2,3-e]indole-2-carboxylic acid (3.12 g, 14.4 mmol) to produce, after flash column chromatography (and without further separation on a second column) a mixture [(2,3-g):(2,3-e)—72:28] of products (2.01 g, 80%) as a white, crystalline solid [$R_f$ 0.46 (SiO$_2$; dichloromethane)] which was used without further purification.

Also collected was 6,7-dihydro-5H-pyrano[3,2-f] indole (250 mg, 10%) as an off-white solid [R$_f$ 0.33 (SiO$_2$; dichloromethane)].

(S)-1-[2-(tert-Butoxycarbonylamino)propyl]-7,8-dihydro-9H-pyrano[2,3-g]indole (S)-1-[2-(tert-Butoxycarbonylamino)propyl]-7,8-dihydro-9H-pyrano[2,3-g]indole was prepared according to the method described in Example 3, using a mixture [(2,3g):(2,3-e)—7:3] of 7,8-dihydro-9H-pyrano[2,3-g]indole and 5,6-dihydro-7H-pyrano[2,3-e]indole (1.34 g, 7.7 mmol) to produce, after purification by flash column chromatography [SiO$_2$; ethyl acetate-heptane (1:4)], the product (890 mg, 35%) as a white solid: IR $\nu_{max}$ (Nujol)/cm$^{-1}$ 3352, 2925, 2855, 1687, 1611, 1528, 1458, 1424, 1367, 1358, 1247, 1167, 1054, 961, 704 and 632; NMR (400 MHz, CDCl$_3$) $\delta_H$ 1.03 (3H, d, J 7 Hz), 1.36 (9H, s), 3.10 (1H, m), 3.18 (1H, m), 3.94 (1H, sept, J 7 Hz), 4.12 (1H, m), 4.15 (2H, dd, J 4.5, 6 Hz), 4.46 (1H, m), 6.35 (1H, d, J 3 Hz), 6.63 (1H, d, J 8.5 Hz), 6.82 (1H, d, J 3 Hz) and 7.27 (1H, d, J 8.5 Hz).

(S)-1-[2-(tert-Butoxycarbonylamino)propyl]-2,3,7,8-tetrahydro-9H-pyrano[2,3-g]indole (S)-1-[2-(tert-Butoxycarbonylamino)propyl]-2,3,7,8-tetrahydro-9H-pyrano[2,3-g]indole was prepared according to the procedure described in Example 3, using (S)-1-[2-(tert-butoxycarbonylamino)propyl]-7,8-dihydro-9H-pyrano[2,3-g]indole (870 mg, 2.63 mmol) with the following modification. After the basification step, the mixture was extracted with chloroform, washed with brine, dried (magnesium sulfate) and concentrated in vacuo to afford the product (860 mg, 98%) as a white solid: mp. 137–140° C.; Found: C, 68.71; H, 8.49; N, 8.39%. C$_{19}$H$_{28}$N$_2$O$_3$ requires: C, 68.65; H, 8.49; N, 8.42%.

(S)-1-(2,3,7,8-Tetrahydro-9H-pyrano[2,3-g]indol-1-yl)-2-propylamine Fumarate (S)-1-(2,3,7,8-Tetrahydro-9H-pyrano[2,3-g]indol-1-yl)-2-propylamine fumarate was prepared according to the method described in Example 3, using (S)-1-[2-(tert-butoxycarbonylamino)propyl]-2,3,7,8-tetrahydro-9H-pyrano[2,3-g]indole (820 mg, 2.47 mmol) with the following modification. After evaporation of the methanol, the residue was partitioned between ether and aqueous sodium hydroxide (2N), the aqueous phase was extracted with ether, dried (magnesium sulfate) and concentrated in vacuo to afford the free amine as a pale yellow oil (572 mg, 100%). The fumarate was formed according to the procedure described in Example 3, giving the product (728 mg, 79%) as a white solid: mp. 168–169° C.; Found: C, 62.02; H, 7.14; N, 8.02%. C$_{14}$H$_{20}$N$_2$O.C$_4$H$_4$O$_4$ requires: C, 62.05; H, 6.94; N, 8.04%.

Example 5

(S)-1-(2,3,7,8-tetrahydrothieno[2,3-g]indol-1-yl)-2-propylamine Fumarate

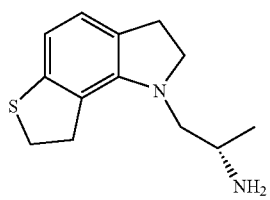

2,3-Dihydrobenzo[b]thiophene, 1,1-dioxide

To a stirred solution/suspension of benzo[b]thiophene, 1,1-dioxide (25.0 g, 0.15 mol) in a mixture of tetrahydrofuran (165 mL) and ethanol (110 mL) under Ar at ambient temperature was added palladium on carbon (10 wt %; 880 mg) and the mixture was shaken under a 20 psi hydrogen atmosphere for 15 min. The reaction mixture was filtered and concentrated in vacuo to afford the product (24.68 g, 98%) as a yellow oil: IR $\nu_{max}$ (Nujol)/cm$^{-1}$ 2925, 2854, 1600, 1456, 1378, 1292, 1266, 1196, 1148, 1120, 1060, 982, 854, 787, 746, 600, 549 and 516; NMR (400 MHz, CDCl$_3$) $\delta_H$ 3.35 (2H, t, J 6.5 Hz), 3.68 (2H, t, J 6.5 Hz), 7.52 (1H, m), 7.55 (1H, m), 7.66 (1H, dt, J 7.5, 1 Hz), 7.74 (1H, d, J 7.5 Hz).

2,3-Dihydrobenzo[b]thiophene

To a stirred solution of 2,3-dihydrobenzo[b]thiophene, 1,1-dioxide (24.62 g, 146 mmol) in tetrahydrofuran (350 mL) under Ar at ambient temperature was added a solution of lithium aluminium hydride (1.0 M in tetrahydrofuran; 161 mL, 161 mmol) dropwise over 10 min, then the mixture was heated at reflux for 30 min. The reaction was allowed to cool to ambient temperature, then quenched by the dropwise addition of water (6.6 mL) followed by 15% aqueous sodium hydroxide (6.6 mL), then water (19.9 mL). The mixture was filtered, diluted with ether, washed with brine, dried (magnesium sulfate) and concentrated in vacuo to afford the crude product. Purification by flash column chromatography (SiO$_2$; heptane) afforded the product (4.80 g, 24%) as a pale yellow oil: R$_f$ 0.35 (heptane); NMR (400 MHz, CDCl$_3$) $\delta_H$ 3.27 (1H, m), 3.28 (1H, d, J 7 Hz), 3.33 (1H, d, J 7 Hz), 3.35 (1H, dd, J 2.5, 4 Hz), 7.00 (1H, dt, J 1.5, 6 Hz), 7.10 (1H, dt, J 1.5, 6 Hz), 7.18 (1H, d, J 7.5 Hz), 7.21 (1H, d, J 7.5 Hz).

2,3-Dihydrobenzo[b]thiophene-5-carboxaldehyde and 2,3-Dihydrobenzo[b]thiophene-7-carboxaldehyde A mixture of 2,3-dihydrobenzo[b]thiophene-5-carboxaldehyde and 2,3-dihydrobenzo[b]thiophene-7-carboxaldehyde was prepared according to the method described in Example 3, using 2,3-dihydrobenzo[b]thiophene (4.8 g, 35.2 mmol) to produce, after purification by flash column chromatography [SiO$_2$; heptane-ether (4:1→2:1)] a mixture [5-CHO:7-CHO (1.3:1)] of aldehyde products (2.55 g, 44%) as a yellow oil which was used without further purification.

Methyl 2-azido-3-(2,3-dihydrobenzo[b]thiophene-5-yl)propenate and Methyl 2-azido-3-(2,3-dihydrobenzo[b]thiophene-7-yl)propenate Methyl 2-azido-3-(2,3-dihydrobenzo[b]thiophene-5-yl)propenate and methyl 2-azido-3-(2,3-dihydrobenzo[b]thiophene-7-yl)propenate were prepared according to the method described in Example 3, using the above mixture (1.3:1) of 2,3-dihydrobenzo[b]thiophene carboxaldehydes and (2.55 g, 15.53 mmol) to produce (without purification by flash column chromatography) a mixture [5-substituted:7-substituted (1.4:1)] of products (3.61 g, 89%) as a pale yellow oil which was used without further purification.

Methyl 7,8-dihydrothieno[2,3-g]indole-2-carboxylate, Methyl 5,6-dihydrothieno[3,2-f]indole-2-carboxylate and Methyl 5,6-dihydrothieno[2,3-e]indole-2-carboxylate Methyl 7,8-dihydrothieno[2,3-g]indole-2-carboxylate, methyl 5,6-dihydrothieno[3,2-f]indole-2-carboxylate and methyl 5,6-dihydrothieno[2,3-e]indole-2-carboxylate were prepared according to the method described in Example 3, using a mixture (1.4:1) of the above 2-azidopropanates (3.61 g, 13.8 mmol), with the following modification. The addition of the substrate to the refluxing xylenes was carried out over 2.5 h, heated for a further 0.5 h, then allowed to cool to ambient temperature. The solvent was removed in vacuo and the crude product was purified by flash column chromatography (SiO$_2$; dichloromethane) to afford a mixture

[(2,3-g):(3,2-f):(2,3-e)—34:44:22] of products (1.92 g, 60%) as a white solid which was used without further purification.

7,8-dihydrothieno[2,3-g]indole-2-carboxylic Acid, 5,6-dihydrothieno[3,2-f]indole-2-carboxylic Acid and 5,6-dihydrothieno[2,3-e]indole-2-carboxylic Acid 7,8-dihydrothieno[2,3-g]indole-2-carboxylic acid, 5,6-dihydrothieno[3,2-f]indole-2-carboxylic acid and 5,6-dihydrothieno[2,3-e]indole-2-carboxylic acid were prepared according to the method described in Example 3, using a mixture (34:44:22) of the above methyl dihydrothienoindole-2-carboxylates (1.84 g, 7.89 mmol) to produce a mixture [(2,3-g):(3,2-f):(2,3-e)—41:35:24] of products (1.65 g, 95%) as a pale green solid which was used without further purification.

7,8-Dihydrothieno[2,3-g]indole, 5,6-dihydrothieno[3,2-f] and 5,6-dihydrothieno[2,3-e]indole 7,8-Dihydrothieno[2,3-g]indole, 5,6-dihydrothieno[3,2-f] and 5,6-dihydrothieno[2,3-e]indole were prepared according to the method described in Example 3, using the above mixture of dihydrothienoindole-2-carboxylic acids (1.64 g, 7.48 mmol), with the following modification. After the mixture had been passed down the heptane-packed column and the phenyl ether flushed-off with heptane, the eluant was increased to heptane-dichloromethane (1:1→1:3) to afford a purple solid. The solid was recrystallised [heptane-isopropyl ether (1:1)] to afford a mixture (2:3) of 7,8-dihydrothieno[2,3-g]indole and 5,6-dihydrothieno[3,2-f]indole (540 mg, 41%) as a pink solid. The filtrate was evaporated to afford a mixture (25:30:45) of 7,8-dihydrothieno[2,3-g]indole, 5,6-dihydrothieno[3,2-f]indole and 5,6-dihydrothieno[2,3-e]indole (644 mg, 49%) as a purple solid which was used without further purification.

(S)-1-[2-(tert-Butoxycarbonylamino)propyl]-7,8-dihydrothieno[2,3-g]indole (S)-1-[2-(tert-Butoxycarbonylamino)propyl]-7,8-dihydrothieno[2,3-g]indole was prepared according to the method described in Example 3, using a mixture (25:30:45) of 7,8-dihydrothieno[2,3-g]indole, 5,6-dihydrothieno[3,2-f]indole and 5,6-dihydrothieno[2,3-e]indole (617 mg, 3.52 mmol) to afford, after purification by flash column chromatography [SiO$_2$; ethyl acetate-heptane (1:3)], the product (200 mg, 17%) as a white solid: IR $\nu_{max}$ (Nujol)/cm$^{-1}$ 3347, 2922, 2855, 1680, 1520, 1460, 1378, 1364, 1314, 1252, 1169, 1056, 884, 798 and 721; NMR (400 MHz, CDCl$_3$) $\delta_H$ 1.08 (3H, d, J 7 Hz), 1.40 (9H, s), 3.45 (2H, dt, J 1.5, 6 Hz), 3.61 (1H, m), 3.72 (1H, m), 3.98 (1H, m), 4.08 (1H, m), 4.39 (2H, m), 6.42 (1H, d, J 3 Hz), 6.90 (1H, d, J 3 Hz) 6.98 (1H, d, J 8 Hz), 7.38 (1H, d, J 8 Hz).

(S)-1-[2-(tert-Butoxycarbonylamino)propyl]-2,3,7,8-tetrahydrothieno[2,3-g]indole (S)-1-[2-(tert-Butoxycarbonylamino)propyl]-2,3,7,8-tetrahydrothieno[2,3-g]indole was prepared according to the method described in Example 3, using (S)-1-[2-(tert-butoxycarbonylamino)propyl]-7,8-dihydrothieno[2,3-g]indole (200 mg, 0.60 mmol) to produce, after purification by flash column chromatography [SiO$_2$; ethyl acetate-heptane (1:4)], the product (138 mg, 69%) as a pale green solid: mp. 170–171.5° C.; Found: C, 64.60; H, 7.72; N, 8.37%. C$_{18}$H$_{26}$N$_2$O$_2$S requires: C, 64.64; H, 7.83; N, 8.37%.

(S)-1-(2,3,7,8-Tetrahydrothieno[2,3-g]indol-1-yl)-2-propylamine Fumarate (S)-1-(2,3,7,8-Tetrahydrothieno[2,3-g]indol-1-yl)-2-propylamine fumarate was prepared according to the method described in Example 3, using (S)-1-[2-(tert-butoxycarbonylamino)propyl]-2,3,7,8-tetrahydrothieno[2,3-g]indole (122 mg, 0.36 mmol) to produce the product (104 mg, 82%) as a white solid: mp. 188–189.5° C. (dec.); Found: C, 57.98; H, 6.33; N, 7.90%. C$_{13}$H$_{18}$N$_2$S.C$_4$H$_4$O$_4$ requires: C, 58.27; H, 6.33; N, 7.99%.

Example 6

(S)-1-(2,3,7,8-Tetrahydro-9H-1,4-dioxino[2,3-g]indol-9-yl)-2-propylamine Fumarate

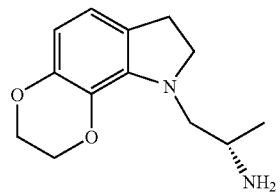

Methyl 2-azido-3-(1,4-benzodioxan-6-yl)propenate

Methyl 2-azido-3-(1,4-benzodioxan-6-yl)propenate was prepared according to the method described in Example 3, using 1,2-benzodioxan-6-carboxaldehyde (4.67 g, 28.5 mmol) to produce the product (3.89 g, 52%) as a pale yellow solid: IR $\nu_{max}$ (Nujol)/cm$^{-1}$ 2925, 2854, 2121, 1710, 1699, 1620, 1608, 1601, 1576, 1508, 1466, 1434, 1381, 1317, 1300, 1265, 1252, 1236, 1211, 1165, 1157, 1125, 1084, 1066, 1050, 967, 952, 920, 906, 888, 862, 840, 805, 774, 756, 725, 663, 616 and 563; NMR $\delta_H$ (400 MHz; CDCl$_3$) 3.39 (1H, s), 4.25–4.31 (4H, m), 6.81 (1H, s), 6.86 (1H, d, J 8.5 Hz), 7.24 (1H, dd, J 8.5, 2.0 Hz) and 7.51 (1H, d, J 2.0 Hz).

Methyl 2,3-dihydro-9H-1,4-dioxino[2,3-g]indole-8-carboxylate

Methyl 2,3-dihydro-9H-1,4-dioxino[2,3-g]indole-8-carboxylate was prepared according to the procedure described in Example 3, using methyl 2-azido-3-(1,4-benzodioxan-6-yl)propenate (3.81 g, 14.58 mmol), with the following modification. The addition of the substrate to the refluxing xylenes was carried out over 5 h, the mixture was heated for a further 0.5 h, then the solvent was removed in vacuo. The resultant crude product was purified by flash column chromatography (SiO$_2$; dichloromethane) to afford the product (1.58 g, 46%) as a white solid: IR $\nu_{max}$ (Nujol)/cm$^{-1}$ 3302, 2927, 2855, 1748, 1712, 1694, 1634, 1589, 1548, 1513, 1455, 1392, 1377, 1320, 1277, 1257, 1200, 1102, 1084, 1019, 990, 935, 910, 875, 835, 824, 802, 788, 773, 748, 742, 685, 634, 596, 583, 562, 546, 534, 486 and 458; NMR $\delta_H$ (400 MHz, CDCl$_3$) 3.92 (1H, s), 4.32–4.39 (4H, m), 6.75 (1H, d, J 8.5 Hz), 7.11–7.15 (2H, m) and 8.90 (1H, br s).

2,3-Dihydro-9H-1,4-dioxino[2,3-g]indole-8-carboxylic Acid 2,3-Dihydro-9H-1,4-dioxino[2,3-g]indole-8-carboxylic acid was prepared according to the method described in Example 3, using methyl 2,3-dihydro-9H-1,4-dioxino[2,3-g]indole-8-carboxylate (1.61 g, 6.90 mmol) to produce, after recrystallisation [ethanol-water (1:2)], the product (1.25 g, 82%) as a pale pink crystalline solid: mp 222–223° C. (dec.); Found: C, 60.06; H, 4.11; N, 6.33%. C$_{11}$H$_9$NO$_4$ requires: C, 60.28; H, 4.14; N, 6.39%.

2,3-Dihydro-9H-1,4-dioxino[2,3-g]indole 2,3-Dihydro-9H-1,4-dioxino[2,3-g]indole was produced according to the method described in Example 3, using 2,3-dihydro-9H-1,4-dioxino[2,3-g]indole-8-carboxylic acid (1.192 g, 5.44 mmol) to produce the product (934 mg, 98%) as a pale yellow oil: NMR $\delta_H$ (400 MHz, CDCl$_3$) 4.27–4.37

(4H, m), 6.65 (1H, d, J 8.5 Hz), 7.01 (1H, d, J 2.0 Hz), 7.07 (1H, d, J 8.5 Hz), 11.52 (1H, s) and 12.65 (1H, br s); Found: C, 68.56; H, 5.12; N, 7.75%. $C_{10}H_9NO_2$ requires: C, 68.56; H, 5.18; N, 7.99%.

(S)-9-[2-(tert-Butoxycarbonylamino)propyl]-(2,3-dihydro-9H-1,4-dioxino[2,3-g]indole (S)-9-[2-(tert-Butoxycarbonylamino)propyl]-(2,3-dihydro-9H-1,4-dioxino[2,3-g]indole was prepared according to the procedure described in Example 3, using 2,3-dihydro-9H-1,4-dioxino[2,3-g]indole (875 mg, 4.99 mmol) to produce, after purification by flash column chromatography [SiO$_2$; ethyl acetate-heptane (1:4→3:7)], the product (1.113 g, 67%) as a white solid: IR $v_{max}$ (Nujol)/cm$^{-1}$ 3420, 3104, 2926, 2825, 1705, 1627, 1583, 1506, 1460, 1434, 1376, 1367, 1352, 1322, 1272, 1257, 1205, 1178, 1160, 1090, 1059, 966, 878, 795, 714, 632 and 492; NMR (400 MHz, CDCl$_3$) $\delta_H$ 1.11 (3H, d, J 6.5 Hz), 1.28 (9H, s), 4.00 (1H, sept, J 7 Hz), 4.21 (1H, m), 4.30 (2H, dt, J 1, 3.5 Hz), 4.36 (2H, dt, J 3.5, 1 Hz), 4.74 (1H, m), 6.35 (1H, d, J 3 Hz), 6.65 (1H, d, J 8.5 Hz), 6.86 (1H, d, J 3 Hz), 7.01 (1H, d, J 8.5 Hz).

(S)-9-[2-(tert-Butoxycarbonylamino)propyl]-2,3,7,8-tetrahydro-9H-1,4-dioxino[2,3-g]indole (S)-9-[2-(tert-Butoxycarbonylamino)propyl]-2,3,7,8-tetrahydro-9H-1,4-dioxino[2,3-g]indole was prepared according to the procedure described in Example 3, using (S)-9-[2-(tert-butoxycarbonylamino)propyl]-(2,3-dihydro-9H-1,4-dioxino[2,3-g]indole (1.09 g, 3.28 mmol) to produce, after purification by flash column chromatography [SiO$_2$; ethyl acetate-heptane (1:4)], the product (896 mg, 81%) as a white solid: mp 129.5–132° C.; Found: C, 64.61; H, 7.87; N, 8.32%. $C_{18}H_{26}N_2O_4$ requires: C, 64.65; H, 7.84; N, 8.37%.

(S)-1-(2,3,7,8-Tetrahydro-9H-1,4-dioxino[2,3-g]indol-9-yl)-2-propylamine Fumarate (S)-1-(2,3,7,8-Tetrahydro-9H-1,4-dioxino[2,3-g]indol-9-yl)-2-propylamine fumarate was prepared according to the procedure described in Example 3, using (S)-9-[2-(tert-butoxycarbonylamino)propyl]-2,3,7,8-tetrahydro-9H-1,4-dioxino[2,3-g]indole (870 mg, 2.60 mmol) to produce the product (723 mg, 79%) as a white solid: mp 173–174° C. (dec.); Found: C, 58.09; H, 6.36; N, 7.95%. $C_{13}H_{18}N_2O_2 \cdot C_4H_4O_4$ requires: C, 58.28; H, 6.33; N, 7.99%.

Example 7

(S)-1-(2,3,6,7,8,9-Hexahydro-1H-benz[g]indol-1-yl)]-2-propylamine, Fumarate

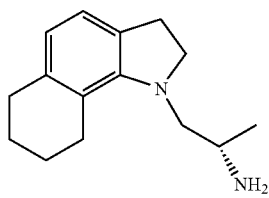

6,7,8,9-Tetrahydro-1H-benz[g]indole-2,3-dione

The benz[g]isatin was prepared in two steps from 5,6,7,8-tetrahydro-1-naphthylamine using the methods described for 1,6,7,8-tetrahydrocyclopenta[g]indole-2,3-dione (G. W. Rewcastle et. al., *J. Med. Chem.,* 1991, 34, 217). The product (54% yield from N-[1-(5,6,7,8-tetrahydronaphthalenyl)]-2-(hydroximino)acetamide) was obtained as an orange solid: mp. 234–235° C. (lit. [U.S. Pat. No. 1,856,210, 1929] 232° C.); NMR $\delta_H$ (400 MHz, DMSO-d$_6$) 1.73 (4H, m), 2.49 (2H, m), 2.73 (2H, m), 6.78 (1H, d, J 7.7 Hz), 7.21 (1H, d, J 7.7 Hz) and 10.92 (1H, s).

6,7,8,9-Tetrahydro-1H-benz[g]indole

To a suspension of lithium aluminium hydride (2.85 g, 75.0 mmol) in dry tetrahydrofuran (150 mL) was added 6,7,8,9-tetrahydro-1H-benz[g]indole-2,3-dione (3.018 g, 15.0 mmol) portionwise over 30 min. The green suspension was heated under reflux for 18 h and then cooled to 0° C. The suspension was treated with water (2.8 mL), 5 N aqueous sodium hydroxide (2.1 mL), and water (9.2 mL), and was stirred for an additional 1 h. The suspension was then filtered, the residue was washed with tetrahydrofuran, and the filtrate then concentrated in vacuo. The residue obtained was purified by column chromatography [SiO$_2$; ethyl acetate-heptane (1:19)] and triturated with hexane to give the title indole (1.58 g, 62%) as a white solid: mp. 93–94° C. (lit. [*Khim. Geterotsikl. Soedin.,* 1978, 14, 634] 89–90° C.); Found: C, 84.25; H, 7.65; N, 8.16%. $C_{12}H_{13}N$ requires: C, 84.17; H, 7.65; N, 8.18%.

(S)-1-[2-(tert-Butoxycarbonylamino)]-6,7,8,9-tetrahydro-1H-benz[g]indole

To a suspension of powdered potassium hydroxide (85%; 2.11 g, 32.0 mmol) in methyl sulfoxide (30 mL) at 40° C. was added 6,7,8,9-tetrahydro-1H-benz[g]indole (1.37 g, 8.0 mmol). The green suspension was stirred at 40° C. for 1 h, and then a solution of (S)-2-(tert-butoxycarbonylamino) propane methanesulfonate (5.07 g, 20.0 mmol) in methyl sulfoxide (10 mL) was added dropwise over 1 h. The suspension was heated at 40° C. for 66 h, poured onto a mixture of ice (150 g) and water (50 mL) and extracted with isopropyl ether (2×50 mL). The combined organic extracts were washed with water (50 mL), dried (sodium sulfate) and concentrated in vacuo. The residue obtained was purified by column chromatography [SiO$_2$; ethyl acetate-heptane (1:1)] and triturated with hexane to give the title carbamate (1.49 g, 57%) as a white solid: mp. 118–119° C.; Found: C, 72.65; H, 8.75; N, 8.45%. $C_{20}H_{28}N_2O_2$ requires: C, 73.14; H, 8.59; N, 8.52%; NMR $\delta_H$ (400 MHz, CDCl3) 7.34 (1H, d, J 8.0 Hz), 6.92 (1H, m), 6.82 (1H, d, J 8.0 Hz), 6.40 (1H, m), 4.4 (1H, br), 4.28 (1H, m, J 6.5 Hz), 3.96 (1H, m, J 6.8 Hz), 3.16 (2H, m), 2.91 (2H, m), 1.89 (2H, m), 1.83 (2H, m), 1.45 (9H, br s) and 1.07 (3H, d, J 6.8 Hz).

(S)-1-[2-(tert-Butoxycarbonylamino)]-2,3,6,7,8,9-hexahydro-1H-benz[g]indole

To a solution of (S)-1-[2-(tert-butoxycarbonylamino)]-6,7,8,9-tetrahydro-1H-benz[g]indole (0.985 g, 3.0 mmol) in acetic acid (50 mL) cooled in ice was added sodium cyanoborohydride (0.60 g, 9.55 mmol) in one portion. The solution was stirred for 18 h and was poured onto a mixture of ice (150 g) and water (50 mL). The suspension was stirred for 15 min and more ice was added. The suspension was basified with ammonium hydroxide (140 mL) and extracted with ethyl acetate (2×100 mL). The combined organic extracts were washed with water (100 mL), dried (magnesium sulfate) and concentrated in vacuo. The residue obtained was purified by column chromatography [SiO$_2$; ethyl acetate:heptane (1:4) to give the title carbamate (0.935 g, 94%) as a pale purple solid: mp. 91–91.5° C.; Found: C, 72.7; H, 9.2; N, 8.4%. $C_{20}H_{30}N_2O_2$ requires C, 72.7; H, 9.15 N, 8.5%; NMR (400 MHz, CDCl3) $\delta_H$ 6.90 (1H, d, J 7.5 Hz), 6.58 (1H, d, J 7.5 Hz), 4.69 (1H, br s), 3.85 (1H, m), 3.42 (2H, m), 3.14 (1H, m), 2.99 (3H, m), 2.77 (2H, m), 2.66 (2H, m), 1.75 (4H, m), 1.44 (9H, s) and 1.26 (3H, d, J 6.6 Hz).

(S)-1-(2,3,6,7,8,9-Hexahydro-1H-benz[g]indol-1-yl)]-2-propylamine Fumarate

To a stirred solution of (S)-1-[2-(tert-butoxycarbonylamino)]-2,3,6,7,8,9-hexahydro-1H-benz[g]indole (0.859 g, 2.60 mmol) in methanol (8.6 mL) was added hydrogen chloride (4 M in dioxan; 6.5 mL, 26 mmol). The solution was stirred for 3 h and was concentrated in vacuo. The oil was partitioned between dichloromethane (25 mL) and 0.5 N aqueous sodium hydroxide (25 mL), and the aqueous phase was extracted with dichloromethane (25 mL). The combined organic phases were washed with water (25 mL), dried (sodium sulfate) and concentrated in vacuo to give an oil which was dissolved in 2-propanol (7 mL) at 40° C. The solution was added dropwise to a solution of fumaric acid (0.377 g, 3.25 mmol) in 2-propanol (7 mL) at 0° C. The white suspension was cooled to 0° C. and filtered. The filter-cake was washed with 2-propanol and ether and dried to give the title compound (0.789 g, 79%) as a white solid: mp. 178–182° C.; Found: C, 65.6; H, 7.6; N, 8.05%. $C_{15}H_{22}N_2 \cdot C_4H_4O_4$ requires C, 65.9; H, 7.6; N, 8.1%; NMR (400 MHz, DMSO-$d_6$) $\delta_H$ 6.84 (1H, d, J 7.5 Hz), 6.52 (1H, d, J 7.5 Hz), 6.44 (2H, s), 3.37 (2H, m), 3.23 (2H, m), 3.00 (1H, m), 2.89 (2H, m), 2.64 (4H, m), 1.65 (4H, m) and 1.26 (3H, d, J 6.5 Hz).

Example 8

(S)-1-[1-(1,2,3,6,7,8-Hexahydrocyclopent[g]indolyl)]-2-propylamine Fumarate

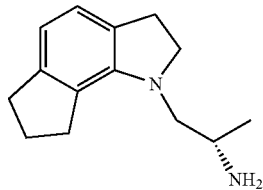

4-Aminoindan Fumarate

4-Aminoindan fumarate was prepared according to the methods described in *J. Chem. Soc., Perkin Trans. 1*, 1975, 519–23.

Cyclopent[g]isatin

Cyclopent[g]isatin was prepared according to the methods described in *J. Med. Chem.*, 1991, 34(1), 217–222. Yield: 5.25 g, 69%, m.p.>330° C.; NMR (400 MHz; DMSO-$d_6$) $\delta_H$ 11.11 (1H, s), 7.30 (1H, d, J 7.6), 6.94(1H, d, J 7.6), 2.88 (2H, t, J 7.5), 2.75 (2H, t, J 7.4), 2.06 (2H, m, J 7.4 and 7.5).

1,6,7,8-Tetrahydrocyclopent[g]indole

A mixture of cyclopent[g]isatin (4.68 g, 25 mmol) and lithium aluminium hydride (4.78 g, 5 equiv) in anhydrous tetrahydrofuran (250 mL) under an argon atmosphere was heated under reflux for 18 h. The mixture was cooled to 0° C. and water (5 mL) then aqueous sodium hydroxide solution (4 mL) followed by water (16 mL) were added sequentially dropwise. The mixture was stirred for 1 h then filtered, washing with tetrahydrofuran (100 mL). To the filtrate was added silica (25 g). The suspension was concentrated in vacuo and purified by column chromatography [SiO$_2$; heptane-ethyl acetate (19:1)] to give the product as an off-white solid (1.64 g, 42%); m.p. 79–81° C. (hexane); Found: C, 83.99; H, 7.05; N, 8.93%. $C_{11}H_{11}N$ requires: C, 84.04; H, 7.05; N, 8.91%.

(S)-tert-Butyl-[2-[1-[1-(1,6,7,8-tetrahydrocyclopent[g]indolyl)]]propyl]carbamate (S)-tert-Butyl-[2-[1-[1-(1,6,7,8-tetrahydrocyclopent[g]indolyl)]]propyl]carbamate was prepared from 1,6,7,8-tetrahydrocyclopent[g]indole using the methods described above for Example 1 (2.1 g, 66%); m.p. 115–116° C. (hexane); Found: C, 72.59; H, 8.43; N, 8.91%. $C_{19}H_{26}N_2O_2$ requires: C, 72.58; H, 8.33; N, 8.91%.

(S)-tert-Butyl-[2-[1-[1-(1,2,3,6,7,8-hexahydrocyclopent[g]indolyl)]]propyl]carbamate (S)-tert-Butyl-[2-[1-[1-(1,2,3,6,7,8-hexahydrocyclopent[g]indolyl)]]propyl]carbamate was prepared from (S)-tert-butyl-[2-[1-[1-(1,6,7,8-tetrahydrocyclopent[g]indolyl)]]propyl]carbamate using the method described above for Example 1 (1.36 g, 86%); m.p. 124° C. (hexane); Found: C, 72.05; H, 8.97; N, 8.82%. $C_{19}H_{28}N_2O_2$ requires C, 72.12; H, 8.92; N, 8.85%.

(S)-1-[1-(1,2,3,6,7,8-Hexahydrocyclopent[g]indolyl)]-2-propylamine Fumarate

To a stirred solution of (S)-tert-butyl-[2-[1-[1-(1,2,3,6,7,8-hexahydrocyclopent[g]indolyl)]]propyl]carbamate (0.31 g, 1.0 mmol) in methanol (5 mL) at 0° C. was added dropwise a solution of hydrogen chloride in dioxan (4 M, 5.0 mL, 20 mmol). The mixture was warmed to room temperature, stirred for 2 h, concentrated in vacuo and partitioned between dichloromethane (25 mL) and aqueous sodium hydroxide solution (5N, 2 mL) in water (10 mL). The separated organic phase was dried (sodium sulfate), concentrated in vacuo and purified by column chromatography [SiO$_2$, chloroform-methanol (19:1)] to give a colourless oil (0.11 g). The oil was dissolved in hot 2-propanol and added to a stirred suspension of fumaric acid (0.068 g) in hot 2-propanol (2 mL). The solution was cooled to room temperature and the emerging precipitate was collected by filtration, washed with 2-propanol and dried in vacuo to give the product as a white solid (0.11 g, 33%); m.p. 182° C. (dec.). Found: C, 65.09; H, 7.29; N, 8.42%. $C_{14}H_{20}N_2 \cdot C_4H_4O_4$ requires: C, 65.04; H, 7.28; N, 8.42%.

Example 9

[2S,3'(R or S)]-1-(3-Ethyl-2,3,7,8-tetrahydrofuro[2,3-g]indol-1-yl)-2-propylamine Fumarate; and Example 10

[2S,3'(S or R)]-1-(3-Ethyl-2,3,7,8-tetrahydrofuro[2,3-g]indol-1-yl)-2-propylamine Fumarate

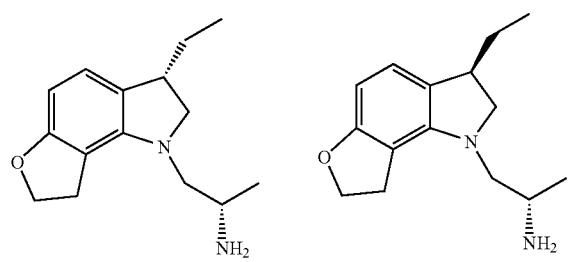

3-Acetyl-7,8-dihydrofuro[2,3-g]indole

To stirred N,N-dimethylacetamide (2.1 mL) under Ar at 0° C. was added phosphorous oxychloride (1.0 mL, 10.7 mmol) dropwise over 10 min. The resultant pale yellow mixture was allowed to warm to ambient temperature, then a solution of 7,8-dihydrofuro[2,3-g]indole (800 mg, 5.0 mmol) in N,N-dimethylacetamide (1.5 mL) was added over 3 min and the mixture was stirred for 2 h. The resultant suspension was heated at 65° C. for 30 min, then cooled in an ice-water bath. Ice (10 g) was added portionwise to the stirred mixture followed by the cautious addition of 20% aqueous sodium hydroxide (10 mL), then water (15 mL). The resultant mixture was heated to reflux for 10 min then cooled to room temperature and diluted with ice-water (50 mL). The suspension was filtered-off and dried to give the crude product (870 mg, 86%) as a beige solid. Recrystallisation from hot ether (10 mL) afforded the product (746 mg, 74%) as a cream-coloured solid: m.p. 233–234.5° C.; NMR (400 MHz, DMSO-d$_6$) $\delta_H$ 2.41 (3H, s), 3.32 (1H, 2H, t, J 8.5 Hz), 4.58 (2H, t, J 8.5 Hz), 6.69 (1H, d, J 8.5 Hz), 7.91 (1H, d, J 8.5 Hz), 8.18 (1H, d, J 3.0 Hz) and 11.76 (1H, br s).

3-Ethyl-7,8-dihydrofuro[2,3-g]indole

To a stirred mixture of 3-acetyl-7,8-dihydrofuro[2,3-g]indole (721 mg, 3.58 mmol) in tetrahydrofuran (25 mL) under an atmosphere of Ar at ambient temperature was added, over 5 min, borane (1.0 M in THF; 18 mL, 18 mmol). The resultant mixture was stirred at ambient temperature for 30 min, then heated to reflux for 2 h before cooling to room temperature. Acetone (25 mL) was added and the mixture was heated to reflux for a further 30 min. The mixture was cooled to room temperature then all solvent was removed in vacuo. Methanol (40 mL) was added, and the mixture was again heated to reflux for 30 min, then cooled to room temperature followed by solvent removal in vacuo. Purification by flash column chromatography [SiO$_2$; ethyl acetate-heptane (1:4)] afforded the product (302 mg, 45%) as a white solid: m.p. 91–92.5° C.; Found: C, 76.90; H, 7.02; N, 7.44%. C$_{12}$H$_{13}$NO requires: C, 76.98; H, 7.00; N, 7.48%.

(S)-1-[2-(tert-Butoxycarbonylamino)propyl]-3-ethyl-7,8-dihydrofuro[2,3-g]indole (S)-1-[2-(tert-Butoxycarbonylamino)propyl]-3-ethyl-7,8-dihydrofuro[2,3-g]indole was prepared according to the method described in Example 1, using 3-ethyl-7,8-dihydrofuro[2,3-g]indole (284 mg, 1.52 mmol). Purification through a short plug of silica (dichloromethane eluant) followed by trituration with hot methanol afforded the product (225 mg, 43%) as a white solid. m.p. 185–186° C. (dec.); NMR (400 MHz, CDCl$_3$) $\delta_H$ 1.11 (3H, d, J 6.5 Hz), 1.29 (3H, t, J 7.5 Hz), 1.41 (9H, br s), 2.70 (2H, qd, J 7.5, 1.0 Hz), 3.43–3.68 (2H, m), 3.89–4.05 (2H, m), 4.10–4.53 (2H, m), 4.60–4.67 (2H, m), 6.69 (2H, m) and 7.31 (1H, d, J 8.5 Hz).

(2'S,3R) and (2'S,3S)-1-[2-(tert-Butoxycarbonylamino)propyl]-3-ethyl-2,3,7,8-tetrahydrofuro[2,3-g]indoles To a stirred solution of (S)-1-[2-(tert-butoxycarbonylamino)propyl]-3-ethyl-7,8-dihydrofuro[2,3-g]indole (209 mg, 0.69 mmol) in acetic acid (20 mL) under Ar at 5° C. was added sodium cyanoborohydride (130 mg, 2.00 mmol), and the resultant mixture was stirred at ambient temperature for 16 h. The reaction was poured onto ice-water (75 mL) and ammonium hydroxide was added portionwise (to pH 9–10). The mixture was extracted with chloroform (3×40 mL). The combined organic extracts were washed with brine (40 mL), dried (MgSO$_4$) and the solvent removed in vacuo to afford the crude products (228 mg, 109%) as a 2:1 mixture of diastereoisomers [as determined by $^1$H-NMR (400 MHz)—by integration of the CHCH$_3$ doublets].

The crude products were dissolved in dichloromethane (1 mL) and were separated into the constituent single diastereomers by repeat injection (50 μL injections) onto a semi-preparative chiral HPLC column [ChiralCel OD, hexane-2-propanol (95:5), 3 mL/min, 210 nm]. This procedure afforded Isomer 1 (95 mg, 45%) as a white solid: LC [ABZ+ (15 cm×4.6 mm; 5 μm); 210 nm; 1 mL/min; methanol-10 mM aqueous ammonium acetate solution (80:20)] 99.1% (4.53 min); MS (ES+) m/z 291 [M+H—(CH$_3$)$_2$C=CH$_2$]$^+$; and Isomer 2 (50 mg, 24%) as a colourless oil (which slowly crystallised to a white solid): LC [ABZ+(15 cm×4.6 mm; 5 μm); 210 nm; 1 mL/min; methanol-10 mM aqueous ammonium acetate solution (80:20)] 98.0% (4.58 min); MS (ES+) m/z 291 [M+H—(CH$_3$)$_2$C=CH$_2$]$^+$.

[2S,3(R or S)]-1-(3-Ethyl-2,3,7,8-tetrahydrofuro[2,3-g]indol-1-yl)-2-propylamine Fumarate Salt formation was carried-out according to the method described in Example 1, affording the title compound (76.5 mg, 77%) as a white solid (fumarate): LC [ABZ+ (15 cm×4.6 mm; 5 μm); 210 nm; 1 mL/min; methanol-10 mM aqueous ammonium acetate solution (70:30)] 98.3% (2.98 min); Found: C, 63.04; H, 7.28; N, 7.79%. C$_{19}$H$_{26}$N$_2$O$_5$ requires: C, 62.97; H, 7.23; N, 7.73%.

[2S,3(S or R)]-1-(3-Ethyl-2,3,7,8-tetrahydrofuro[2,3-g]indol-1-yl)-2-propylamine Fumarate Salt formation was carried-out according to the method described in Example 1, affording the title compound (37.6 mg, 62%) as a white solid (1.5 fumarate): NMR (400 MHz, DMSO) $\delta_H$ 0.90 (3H, t, J 7.5 Hz); 1.23 (3H, d, J 6.5 Hz); 1.36–1.50 (1H, m); 1.65–1.77 (1H, m); 2.93–3.04 (2H, m); 3.08–3.31 (4H, m); 3.32–3.44 (1H, m); 3.45–3.55 (1H, m); 4.36–4.47 (2H, m); 6.60 (1H, d, J 7.5 Hz); 6.48 (3H, s); 6.74 (1H, d, J 7.5 Hz) and 2.8–4.6 (very broad hump—NH$_3^+$): LC [ABZ+ (15 cm×4.6 mm; 5 μm); 210 nm; 1 mL/min; methanol-10 mM aqueous ammonium acetate (70:30)] 97% (3.06 min).

Example 11

(S)-2-[6-(acetyl)-1-(2,3,6,7,8,9-hexahydro-pyrrolo[2,3-f]quinolinyl)]-2-propylamine Fumarate

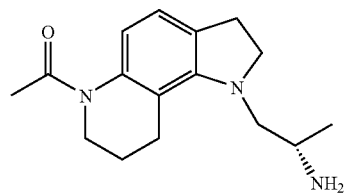

(R)-1-[1-(1H-Pyrrolo[2,3-f]quinolinyl)]-propan-2-ol

A mixture of sodium hydride (60%, 0.76 g, 18.5 mmol) and tetrahydrofuran (30 mL) was cooled to 0° C. under Ar. A solution of 1H-pyrrolo[2,3-f]quinoline (G. Bartoli, G. Palmieri, M. Bosco and R. Dalpozzo, *Tetrahedron Letters*, 1989, 30, 2129–2132) (2.5 g, 14.8 mmol) and tetrahydrofuran (20 mL) was added and the mixture was left at 0° C. for 1 h. (R)-Propylene oxide (2.1 mL, 30 mmol) was added and the mixture was left at room temperature for 48 h. Saturated aqueous ammonium chloride solution (100 mL) was added and the mixture was extracted with ether (3×100 mL), the extracts were combined, washed with brine (2×100 mL), dried (MgSO$_4$), concentrated in vacuo and purified by column chromatography (SiO$_2$; ether) to give the product (0.61 g, 18% yield) as a pale yellow oil: IR $v_{max}$ (Nujol)/cm$^{-1}$ 3106, 1361, 1117, 826, 805, and 731; NMR $\delta_H$ (400 MHz, CDCl$_3$) 1.35 (3H, d, J 6.5 Hz), 2.76 (1H, br), 4.33 (1H, m), 4.44 (1H, m), 4.56 (1H, m), 6.64 (1H, d, J 3.0 Hz), 7.20 (1H, d, J 3.0 Hz), 7.30 (1H, dd, J 8.5 and 4.5 Hz), 7.71 (1H, d, J 9.0 Hz), 7.87 (1H, d, J 9.0 Hz), 8.52 (1H, d, J 8.5 Hz) and 8.67 (1H, m).

(S)-1-(2-Azidopropyl)-1H-pyrrolo[2,3-f]quinoline

A stirred mixture of (R)-1-[1-(1H-pyrrolo[2,3-f]quinolinyl)]-propan-2-ol (0.58 g, 2.6 mmol), dichloromethane (10 mL) and triethylamine (0.4 mL, 2.8 mmol) was cooled to 0° C. Methanesulfonyl chloride (0.2 mL, 2.8 mmol) was added and the yellow mixture was stirred at room temperature for 1 h. Brine (50 mL) was added and the mixture was extracted with dichloromethane (3×50 mL). The extracts were combined, washed with brine (50 mL), dried ($MgSO_4$) and concentrated in vacuo to give a pale yellow solid (0.76 g), which was added to a mixture of DMF (10 mL) and sodium azide (0.3 g, 4.8 mmol). The mixture was heated to 70° C. and stirred for 16 h then cooled to room temperature. Brine (50 mL) was added and the mixture was extracted with ether (3×50 mL), the extracts were combined, washed with brine (50 mL), dried ($MgSO_4$), concentrated in vacuo and purified by column chromatography [$SiO_2$; ethyl acetate-hexane (1:1)] to give the product (0.32 g, 53% yield) as a pale yellow oil: IR $v_{max}$ (liquid film)/cm$^{-1}$ 2119, 1356, 1259, 826, 807, 734, and 696; NMR $\delta_H$ (400 MHz, $CDCl_3$) 1.37 (3H, d, J 6.5 Hz), 4.0 (1H, m), 4.50 (2H, m), 6.70 (1H, d, J 3.0 Hz), 7.17 (1H, d, J 3.0 Hz), 7.46 (1H, dd, J 8.5 and 4.5 Hz), 7.80 (1H, d, J 9.0 Hz), 7.94 (1H, J 8.5 Hz), 8.47 (1H, d, J 8.5 Hz) and 8.85 (1H, d, J 4.5 Hz).

(S)-1-[2-(tert-Butoxycarbonylamino)propyl]-1H-pyrrolo[2,3-f]quinoline

A mixture of (S)-1-(2-azidopropyl)-1H-pyrrolo[2,3-f]quinoline (14.9 g, 59.4 mmol), ethanol (200 mL) and platinum(IV)oxide (0.5 g) was stirred under an hydrogen atmosphere for 36 h. The mixture was filtered through celite®, washing with diethyl ether (2×200 mL) and the filtrate was concentrated in vacuo to give a pale green oil. Water (60 mL) and 2-methyl-2-propanol (60 mL) were added, the mixture was stirred at room temperature for 10 min then freshly crushed sodium hydroxide (9.4 g, 0.23 mol) was added and the mixture was stirred for a further 5 min. Di-tert-butyl dicarbonate (12.8 g, 58.6 mmol) was added and the mixture was left to stir at room temperature for 16 h. Water (100 mL) was added and the mixture was extracted with ethyl acetate (3×30 mL), the extracts were combined washed with brine (2×), dried ($MgSO_4$), filtered, concentrated in vacuo and purified by column chromatography [$SiO_2$; ethyl acetate-heptane (1:8)] to give the title compound (10.3 g, 53%) as a pale brown solid: m.p. 185° C.; $\delta_H$ (400 MHz, $CDCl_3$) 1.13 (3H, s), 1.44 (9H, s), 4.16–4.27 (2H, m), 4.49–4.56 (1H, m), 4.91–5.01 (1H, m), 6.65–6.66 (1H, d, J 1 Hz), 7.12–7.13 (1H, d, J 2.5 Hz), 7.48–7.54 (1H, m), 7.80–7.82 (1H, d, J 9 Hz), 7.91–7.94 (1H, d, J 9 Hz), 8.83–8.86 (1H, m) and 9.05 (1H, brs).

(S)-1-[2-(tert-Butoxycarbonylamino)propyl]-1H-6,7,8,9-tetrahydro-pyrrolo[2,3-f]quinoline A mixture of (S)-1-[2-(tert-butoxycarbonylamino)propyl]-1H-pyrrolo[2,3-f]quinoline (5 g, 15.4 mmol), 10% palladium on activated carbon (0.5 g) and ethanol (30 mL) was shaken under an hydrogen atmosphere (50 psi) for 4 h. The mixture was filtered through celite®, washing with diethyl ether (3×50 mL) and concentrated in vacuo to give a green oil. Column chromatography [$SiO_2$; ethyl acetate-heptane (1:4)] gave the title compound (1.02 g, 20%) as a colourless solid: IR $v_{max}$ (Nujol)/cm$^{-1}$ 3370, 1690, 1523, 1460, 1223, 1173, 1056 and 700; NMR $\delta_H$ (400 MHz, $CDCl_3$) 1.08 (3H, d, J 6.5 Hz), 1.39 (9H, s), 2.01–2.07 (2H, m), 3.08–3.21 (2H, m), 3.28–3.30 (2H, m), 3.95–4.00 (1H, m), 4.15–4.39 (1H, m), 4.39 (2H, brs), 6.20 (1H, d, J 3.5 Hz), 6.37 (1H, d, J 9 Hz), 6.77 (1H, d, J 3.5 Hz) and 7.21 (1H, d, J 9 Hz).

(S)-6-Acetyl-1-[2-(tert-butoxycarbonylamino)propyl]-1H-6,7,8,9-tetrahydropyrrolo[2,3-f]quinoline To a stirred mixture of (S)-1-[2-(tert-butoxycarbonylamino)propyl]-1H-6,7,8,9-tetrahydro-pyrrolo[2,3-f]quinoline (0.9 g, 2.7 mmol) and toluene (15 mL) was added acetic anhydride (0.3 mL, 3.2 mmol). The mixture was heated under reflux for 1 h, cooled to room temperature then concentrated in vacuo and purified by column chromatography [$SiO_2$; ethyl acetate-heptane (1:1)] to give the title compound (0.84 g, 84%) as a colourless foam; IR $v_{max}$ (nujol)/cm$^{-1}$ 1706, 1631, 1458, 1378, 1056 and 723; NMR $\delta_H$ (400 MHz, $CDCl_3$) 1.09 (3H, d, J 6.5 Hz), 1.38 (9H, s), 2.01–2.11 (2H, m), 2.17 (3H, s), 3.05–3.10 (1H, m), 3.12–3.18 (1H, m), 3.83–3.86 (2H, m), 3.94–4.09 (1H, m), 4.20–5.07 (3H, m), 6.45–6.46 (1H, m), 6.88–6.90 (1H, m), 6.98–6.99 (1H, m) and 7.31–7.36 (1H, d, J 9 Hz).

(S)-6-Acetyl-1-[2-(tert-butoxycarbonylamino)propyl]-1H-2,3,6,7,8,9-hexahydropyrrolo[2,3-f]quinoline (S)-6-Acetyl-1-[2-(tert-butoxycarbonylamino)propyl]-1H-2,3,6,7,8,9-hexahydropyrrolo[2,3-f]quinoline was prepared from (S)-6-acetyl-1-[2-(tert-butoxycarbonylamino)propyl]-1H-6,7,8,9-tetrahydropyrrolo[2,3-f]quinoline according to the method described in Example 1 to give a pale yellow oil (0.54 g, 91%); IR $v_{max}$ (DCM smear)/cm$^{-1}$ 1707, 1633, 1251, 1169 and 736; NMR $\delta_H$ (400 MHz, $CDCl_3$) 1.26–1.28 (3H, d, J 6 Hz), 1.44 (9H, s), 1.83–1.99 (2H, m), 2.17 (3H, s), 2.53–2.71 (2H, m), 2.94–3.26 (4H, m), 3.42–3.59 (2H, m), 3.67–3.82 (2H, m), 3.86–3.97 (1H, m), 4.66 (1H, brs), 6.49–6.61 (1H, m), and 6.92–6.95 (1H, d, J 8 Hz).

(S)-2-[6-(acetyl)-1-(2,3,6,7,8,9-hexahydro-pyrrolo[2,3-f]quinolinyl)]-2-propylamine Fumarate (S)-2-[6-(acetyl)-1-(2,3,6,7,8,9-hexahydro-pyrrolo[2,3-f]quinolinyl)]-2-propylamine fumarate was prepared from (S)-6-acetyl-1-[2-(tert-butoxycarbonylamino)propyl]-1H-2,3,6,7,8,9-hexahydropyrrolo[2,3-f]quinoline according to the method described in Example 1 to give the product as a colourless solid (0.37 g, 74%): m.p. 230° C. (dec.); NMR $\delta_H$ (400 MHz, DMSO-$d_6$) 1.32–1.33 (3H, d, J 6.5 Hz), 1.76–1.98 (2H, m), 2.15 (3H, s), 2.61–2.79 (2H, m), 2.91–3.78 (XH, m), 6.53 (2H, s), 6.79–6.88 (1H, m) and 7.01–7.03 (1H, d, J 7.5 Hz).

What is claimed is:

1. A chemical compound of formula (I):

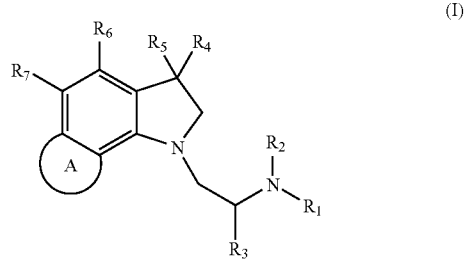

wherein:
$R_1$ and $R_2$ are independently selected from hydrogen and alkyl;
$R_3$ is alkyl;
$R_4$ and $R_5$ are selected from hydrogen and alkyl;
$R_6$ and $R_7$ are independently selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl; and A is a 5 or 6-membered ring containing one heteroatom selected from N, wherein the atoms of the ring A, other than the unsaturated carbon atoms of the phenyl ring to which the ring A is fused, are saturated or unsaturated, or a pharmaceutically acceptable salt, or addition compound thereof.

2. A compound according to claim 1, wherein A is 6 membered ring.

3. A compound according to claim 1, wherein $R_1$ and $R_2$ are independently selected from H and lower alkyl.

4. A compound according to claim 1, wherein $R_1$ and $R_2$ are hydrogen.

5. A compound according to claim 1, wherein $R_3$ is loweralkyl.

6. A compound according to claim 1, wherein $R_3$ is methyl.

7. A compound according to claim 1, wherein $R_4$ and $R_5$ are independently selected from hydrogen and lower alkyl.

8. A compound according to claim 1, wherein $R_6$ and $R_7$ are independently selected from hydrogen and lower alkyl.

9. A compound according to claim 1, wherein one or more of $R_4$ to $R_7$ is/are hydrogen.

10. A compound according to claim 1, wherein A is partially unsaturated.

11. A pharmaceutical composition comprising a compound of formula (I) according to claim 1 in combination with a pharmaceutically acceptable carrier or excipient.

* * * * *